US012808861B2

(12) United States Patent
Ding et al.

(10) Patent No.: US 12,808,861 B2
(45) Date of Patent: Nov. 24, 2026

(54) LATERAL FLOW ASSAY AND VERTICAL FLOW ASSAY

(71) Applicant: Essenlix Corporation, Monmouth Junction, NJ (US)

(72) Inventors: Wei Ding, Princeton, NJ (US); Stephen Y. Chou, Princeton, NJ (US); Wu Chou, Basking Ridge, NJ (US); Ji Wang, Bridgewater, NJ (US); Chen Ji, Bound Brook, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 935 days.

(21) Appl. No.: 17/775,580

(22) PCT Filed: Nov. 9, 2020

(86) PCT No.: PCT/US2020/059754

§ 371 (c)(1),
(2) Date: May 9, 2022

(87) PCT Pub. No.: WO2021/092595

PCT Pub. Date: May 14, 2021

(65) Prior Publication Data

US 2022/0404342 A1 Dec. 22, 2022

Related U.S. Application Data

(60) Provisional application No. 62/932,123, filed on Nov. 7, 2019.

(51) Int. Cl.

*G01N 33/52* (2006.01)
*G01N 21/25* (2006.01)
(Continued)

(52) U.S. Cl.

CPC ......... *G01N 33/521* (2013.01); *G01N 21/251* (2013.01); *G01N 21/27* (2013.01); *G01N 21/78* (2013.01); *G01N 2021/7759* (2013.01)

(58) Field of Classification Search

CPC .... G01N 33/521; G01N 21/251; G01N 21/27; G01N 21/78; G01N 2021/7759;
(Continued)

(56) References Cited

U.S. PATENT DOCUMENTS

2009/0211345 A1 8/2009 Nahm et al.
2010/0045789 A1 2/2010 Fleming et al.
(Continued)

FOREIGN PATENT DOCUMENTS

WO 2005066624 A1 7/2005
WO 2018140568 A1 8/2018

OTHER PUBLICATIONS

International Search Report and Written Opinion of the International Searching Authority established by the ISA/KR completed on Mar. 23, 2021, for PCT/US2020/059754.

*Primary Examiner* — Dennis White

(57) ABSTRACT

Disclosed is a device including a substrate having a plurality of detection areas to receive at least a portion of a sample having an analyte or suspected of having an analyte and at least one reference marker adjacent to at least one of the detection areas, wherein each of the detection areas detects a specific analyte and the at least one reference marker defines a scale mark, a shape mark, a color mark, or a combination thereof. Also disclosed is an imaging system and method for using the device and imaging system.

20 Claims, 9 Drawing Sheets

(51) Int. Cl.
*G01N 21/27* (2006.01)
*G01N 21/77* (2006.01)
*G01N 21/78* (2006.01)

(58) Field of Classification Search
CPC ....... G01N 2021/8488; G01N 21/8483; G01N 33/54366; B01L 2200/148; B01L 2300/028; B01L 2300/0825; B01L 3/5023
See application file for complete search history.

(56) References Cited

U.S. PATENT DOCUMENTS

| | | | | |
|---|---|---|---|---|
| 2016/0051980 | A1* | 2/2016 | Hong .................... | B01L 3/5023 506/39 |
| 2017/0184506 | A1* | 6/2017 | Patel ...................... | G01N 21/78 |
| 2017/0370930 | A1 | 12/2017 | Bearinger et al. | |
| 2018/0196037 | A1 | 7/2018 | Polwart et al. | |

* cited by examiner

| Parameters | FDA Error Allowance (95% CI) | N | Min (mg/dL) | Max (mg/dL) | Essenlix iMOST vs. Commercial Instruments* | | |
|---|---|---|---|---|---|---|---|
| | | | | | Average Δ | Average \|Δ\| | CC (R) |
| Cholesterol | 10 % | 11 | 102 | 270 | 0.2 % | 6.6 % | 97 % |
| HDL Cholesterol | 30 % | 11 | 28 | 94 | -0.2 % | 5.8 % | 98 % |
| Triglycerides | 25 % | 11 | 50 | 230 | 0.6 % | 10 % | 96 % |

LATERAL FLOW ASSAY AND VERTICAL FLOW ASSAY

CROSS-REFERENCING

This application is a National Stage entry (§ 371) application of International Application No. PCT/US2020/059754, filed on Nov. 9, 2020, which claims the benefit of U.S. Provisional Patent Application No. 62/932,123, filed on Nov. 7, 2019, which is incorporated herein in its entirety for all purposes.

The entire disclosure of each publication or patent document mentioned herein is incorporated by reference.

FIELD

The present application relates to a device, system, and method for improving a lateral flow assay, a vertical flow assay for measuring a sample, or both.

BACKGROUND

The present application relates to a device, system, and method for improving a lateral flow assay, a vertical flow assay for measuring a sample, or both.

In a traditional lateral flow assay and a traditional vertical flow assay for measuring an analyte in a sample, the assay reaction regions are often detected using a lamp-sum optical signal. However, a lump-sum optical signal can have large errors, caused by air bubble, unevenness in reactions, or other imperfect conditions during the assay. Furthermore, an optical system for a lateral flow assay and a vertical flow assay may change from a run to run or day to day, leading to additional errors in assay test results. The present invention is to provide, among other things, a solution to the two aforementioned problems.

SUMMARY

One aspect of the present invention is to improve the test accuracy of a lateral flow assay and/or a vertical flow assay by using high resolution imaging methods to sub-divide the assay reaction areas into a plurality of sub-assay reaction area and analyze each of the sub-assay area.

Another aspect of the present invention is to improve the test accuracy of a lateral flow assay and/or a vertical flow assay by providing additional reference marks, either on the sample holder and/or the adaptor (the device that connect the sample holder to the imager), that can calibrate the optical system (calibrating the light spectrum, image scale, image distortion, or image color uniformity).

In one or more embodiment, the present invention provides:

A device, comprising:

a substrate having a plurality of detection areas to receive at least a portion of a sample having an analyte or suspected of having an analyte; and at least one reference marker adjacent to at least one of the of detection areas, wherein:

each of the detection areas detects a specific analyte; and the at least one reference marker is a scale marker, a shape marker, a color marker, or a combination thereof.

An system for imaging a sample and measuring an analyte in the sample, comprising:

the above device; and an imager for capturing an image of at least one of the detection areas and at least one reference marker; and an image analyzer for measuring the analyte that analyzes the image of at least one of the detection areas and at least one reference marker.

An assay method for measuring an analyte in a sample, comprising:

contacting the abovementioned device and a sample having an analyte or suspected of having an analyte;

imaging the substrate having a plurality of detection areas that have been contacted by the sample after a period of time to form an image in the abovementioned imaging system; and analyzing the image and at least one reference marker.

The disclosed device, system, and methods of the present invention provide an improved platform for accomplishing an improved vertical flow assay (VFA) or an improved lateral flow assay (LFA).

The disclosed device, system, and methods of the present invention can accomplish the improved assay using, for example, imperfect samples, simple but imperfect optical components, poor control (i.e., uncertainty) with respect to the sample and camera position, uncertainty in lighting (i.e., both intensity and position), and camera imperfections.

The disclosed device, system, and methods of the present invention can accomplish the improved assay using, for example, reference structures on surface of the assay area to provide, for example, a spectrum and intensity of a reference light or illumination source, the scale, the focusing, the distortion, and like considerations.

The disclosed device, system, and methods of the present invention can accomplish the improved assay using, for example, imperfect samples (e.g., having impurities or having contaminants or not uniform flowing) and imperfect assay pads, which imperfections can lead to poor color and poor intensity uniformity.

The poor color uniformity of an individual sample or a large group of samples can be compensated for by a color reference.

The disclosed device, system, and methods can adapt to the abovementioned imperfections or overcome the imperfections with, for example, enhanced referencing and enhanced imaging and analysis, to provide an improved assay such as on a qualitative basis, on a quantitative basis, or both.

BRIEF DESCRIPTION OF THE DRAWINGS

The drawings if any, described below, are for illustration purposes only. In some Figures, the drawings are in scale and not to scale in other Figures. For clarity purposes, some elements are enlarged when illustrated in the Figures. The drawings are not intended to limit the scope of the disclosure.

DETAILED DESCRIPTION OF EXEMPLARY EMBODIMENTS

The following detailed description illustrates certain embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

Definitions

"Lateral" refers to a linear configuration or strip where a liquid sample can be applied on one end of the strip and the analyte collection and analysis area is elsewhere on the strip (see Lateral Flow Test on wikipedia.org for background information).

"Vertical" refers to a stacked or layered configuration where a liquid sample can be applied on the top of the stack or layers or bands, and the analyte collection and analysis area is in or on areas or surfaces between the top and the bottom of the stack or layers or bands. The stack or layers or bands can have one or more intermediate layers that are substantially permeable to the analyte and all or a portion of the liquid of the liquid sample. One or more of the intermediate layers can be impermeable to one or more entities that can compete with or confound the analysis of the analyte such as contaminates (e.g., dust particles, hair). One or more of the intermediate layers can interact with the analyte to permit an enhanced assay which is qualitative, quantitative, or both

Multiplexing Assay in One VFA or One LFA Device

A vertical flow assay (VFA) or lateral flow assay (LFA) device can have more than one assay in the detection area.

Figure 1:
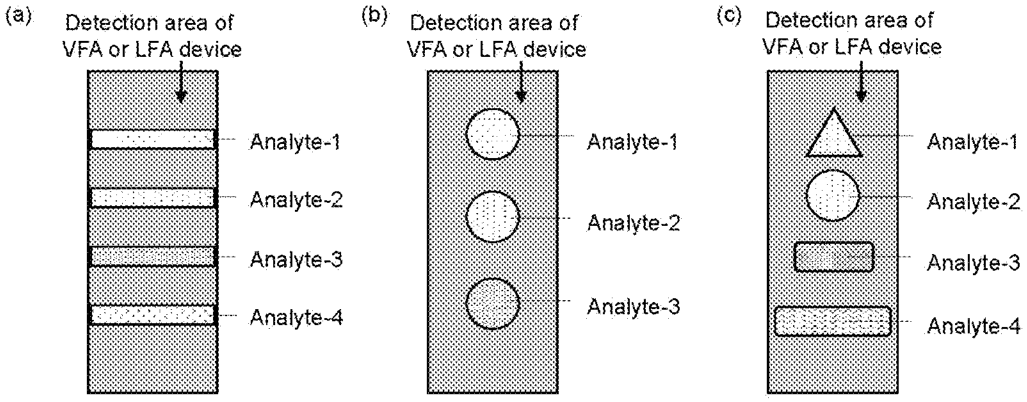
FIG. 1 shows example detection areas of a vertical flow assay ("VFA") or lateral flow assay ("LFA") device having: (a) 4 bar areas for 4 analytes; (b) 3 round areas for 3 analytes; and (c) 4 differently shaped areas for 4 analytes.

Referring to the Figures, FIG. 1 is an example of detection areas of a VFA (vertical flow assay) or LFA (lateral flow assay) device having, for example: (a) 4 bar areas for 4 analytes; (b) 3 round or circular areas for 3 analytes; and (c) 4 different shaped areas for 4 analytes.

The shape, distance, or size of each detection area can be same or different.

In some embodiment, one of the detection areas for one assay has a shape selected from round, polygonal, circular, square, rectangular, oval, elliptical, and like shapes, or any super-positional combination thereof.

In some embodiment, one of the detection areas for one assay has a size of 0.1 mm, 0.2 mm, 0.5 mm, 1 mm, 2 mm, 5 mm, 10 mm, 20 mm, and like size dimensions, or intermediate values or ranges.

In some embodiment, one of the detection areas for one assay has a preferred size of 0.5 mm, 1 mm, 2 mm, 5 mm, 10 mm, and like size dimensions, or intermediate values or ranges.

In some embodiment, the distance between detection areas is 0.1 mm, 0.2 mm, 0.5 mm, 1 mm, 2 mm, 5 mm, 10 mm, 20 mm, or intermediate values or ranges.

In some embodiment, the detection method is an enzymatic reaction assay.

In some embodiment, the detection method is an immunosorbent assay.

In some embodiment, the detection method is a colorimetric method, a fluorescence method, or like color or light detection.

In some embodiment, the detection probe is made of colorimetric dye, fluorescence dye, latex beads, gold nanoparticles, or others.

In some embodiment, the vertical flow assay (VFA) or lateral flow assay (LFA) device is made of paper, cellulose, plastic, polymer, metal and others.

In some embodiment, the vertical flow assay (VFA) or lateral flow assay (LFA) device has more than one layer of material, wherein one of the layers is for imaging.

In some embodiment, the vertical flow assay (VFA) or lateral flow assay (LFA) device performs function and assay including but not limited to blood cell filtering, colorimetric assay, turbidity assay, immunoassay, nucleic acid hybridization assay, nucleic acid amplification assay, electroluminescent assay.

Imaging Based Detection System

Figure 2:
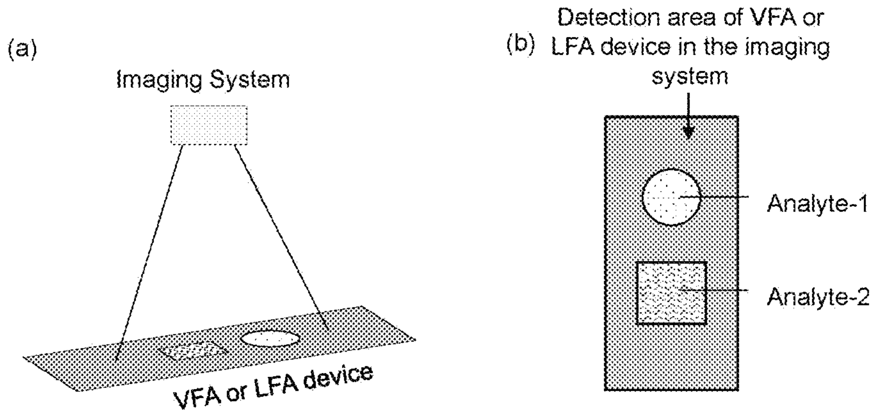
FIG. 2 shows an example of: (a) an image detection system having an imaging device over a VFA or LFA test strip which system captures the image of the detection area on the device; and (b) the captured image and detection area of analytes in the VFA/LFA imaging system.

FIG. 2 is example of the imaging detection system: (a) that consists of the imaging device over a VFA or LFA test strip that captures the image of the detection area on device; and (b) shows an example of the captured image and detection area of analytes in the VFA or LFA imaging system.

In some embodiment, the imaging device consist of a camera and a lighting source.

In some embodiment, the imaging device consist of a lens or a set of lenses.

In some embodiment, the imaging device can provide one or more useful functions such as imaging, data processing, image or data storage, sample illumination, remote communications or reporting, and like functions, or a combination thereof.

In some embodiment, one dimension of the field of view (FOV) of the imaging device is 0.1 mm, 0.2 mm, 0.5 mm, 1 mm, 2 mm, 5 mm, 10 mm, 20 mm, 50 mm, or intermediate values and ranges.

In some embodiment, one dimension of the field of view (FOV) of the imaging device is preferred to be 1 mm, 2 mm, 5 mm, 10 mm, 20 mm, or intermediate values and ranges.

In some embodiment, the light source includes an optical fiber transporter with side light leakage and illumination.

In some embodiment, the imaging system has a resolution of 1 um, 2 um, 5 um, 10 um, 20 um, 100 um, 200 um, or intermediate values and ranges.

In some embodiment, the imaging system has a preferred resolution of 1 um, 2 um, 5 um, 10 um, or intermediate values and ranges.

In some embodiment, the imaging system has a resolution of 1/10000, 1/1000, 1/100, 1/10 of the size of the detection areas for one assay, or intermediate values and ranges.

In some embodiment, the imaging system has a resolution of 1/100, 1/50, 1/20, 1/10, 1/5 of the size of the imperfection size in the assay, or intermediate values and ranges.

In some embodiment, the imaging system can have a filter to enhance and select certain wavelengths of light.

In some embodiment, the illumination system can have elements to make the light uniform and illumination area enlarged.

In some embodiment, the imaging system can have a set of polarizers to enhance the imaging quality or image contrast.

In some embodiment, the imaging system uses a RAW file format in processing the recorded image or photo taken.

In some embodiment, the imaging system consists a smartphone.

In some embodiment, the imaging system consists of a set of optics to correct the distortion, color, brightness, uniformity of the photo taken.

Standardized Testing Reference

A vertical flow assay (VFA) or lateral flow assay (LFA) device can have more than one assay in the entire detection area or in separated individual detection areas, and the device can have one or more reference markers.

Figure 3:
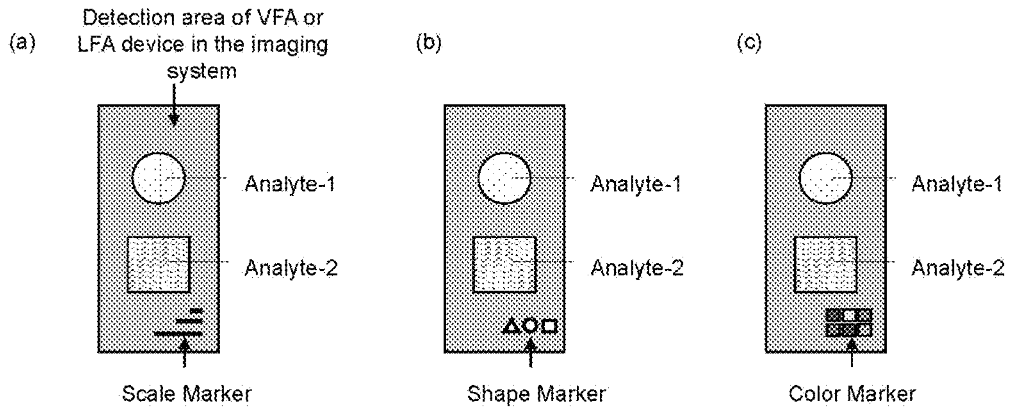
FIG. 3 shows three examples of an image detection area having a reference marker in the VFA or LFA device in the imaging system: (a) a detection area of two captured analytes and a scale marker as a size or distance reference; (b) a detection area of two captured analytes and a shape marker as a shape reference; and (c) a detection area of two captured analytes and a color marker as a color reference.

FIG. 3 shows three example detection areas of a VFA (vertical flow assay) or LFA (lateral flow assay) device having: (a) a scale marker for analytes; (b) a shape marker for analytes; or (c) a color marker for analytes.

In some embodiment, one of the scale markers has a length of 2 um, 10 um, 20 um, 50 um, 100 um, or an intermediate value or range.

In some embodiment, one of the scale markers has a length of 0.1 mm, 0.2 mm, 0.5 mm, 1 mm, 2 mm, 5 mm, 10 mm, or an intermediate value or range.

In some embodiment, the scale markers have size accuracy less than 1%, 2%, 3%, 5%, or an intermediate value or range.

In some embodiment, one of the shape markers has a shape selected from round, polygonal, circular, square, rectangular, oval, elliptical, or any super-positional combination thereof.

In some embodiment, one of the color markers has a color that matches the colorimetric assay in the device.

In some embodiment, one of the color marks in the color marker has a color that matches the central absorption wavelength of a reactive dye or the color of the dye in the device.

In some embodiment, one of the color marks in the color marker has a color that matches the central absorption wavelength of a reactive dye or the color of the dye in the device within the wavelength of 10 nm, 20 nm, 30 nm, 50 nm or an intermediate value or range.

In some embodiment, one of the color marks in the color marker has a color that has a central absorption wavelength within the range of 400 nm to 700 nm.

In some embodiment, one of the color marks in the color marker has a color that has more than one central absorption wavelength of from 400 nm to 700 nm.

In some embodiment, at least one of the color marks in the color marker has a color that has an absorption wavelength bandwidth selected from 20 nm, 50 nm, 80 nm, 100 nm, 150 nm, 200 nm, or an intermediate value or range.

In some embodiment, there is periodic structures as pillars within the detection area as the scale marker, color marker, orientation marker and shape marker.

In some embodiment, the spacers in the Q-Cards within the detection area are also used as the scale marker, color marker, orientation marker and shape marker.

In some embodiment, the periodic pillar or spacer has a period of 10 um, 20 um, 30 um, 50 um, 100 um, 150 um, 200 um, 500 um, or an intermediate value or range.

In some embodiment, the periodic pillar or spacer has a preferred period of 50 um, 100 um, 120 um, 150 um, or an intermediate value or range.

In some embodiment, the periodic pillar or spacer has a size of 2 um, 5 um, 10 um, 20 um, 30 um, 50 um, 100 um, 150 um, 200 um, 500 um, or an intermediate value or range.

In some embodiment, the periodic pillar or spacer has a preferred size of 10 um, 20 um, 30 um, 50 um, or an intermediate value or range.

In some embodiment, there is at least 4 periodic pillar or spacer in the field of view of the imager.

Reduced Image-Based Assay Error Using Image Recognition Software

It is desirable to have the flow assay reaction and test results free from imperfections, inhomogeneities, or contamination. For example, in the resulting image, inhomogeneous color generation and incomplete color generation can cause inaccurate interpretation of the analyte concentration, the quantity, and the type of analyte. Accordingly, an automatic image analyzing system that can discern, for example, a non-uniform image, a signal boundary, an image defection (e.g., bubble or aggregation), and like inhomogeneities or incompletions, is desirable.

In a traditional method, the signal is "lump sum", read by a photo-detector and without imaging or fine grain image analysis. Accordingly, a traditional method cannot distinguish, analyze, or correct for the abovementioned imperfections, inhomogeneities, or contamination.

Figure 4:
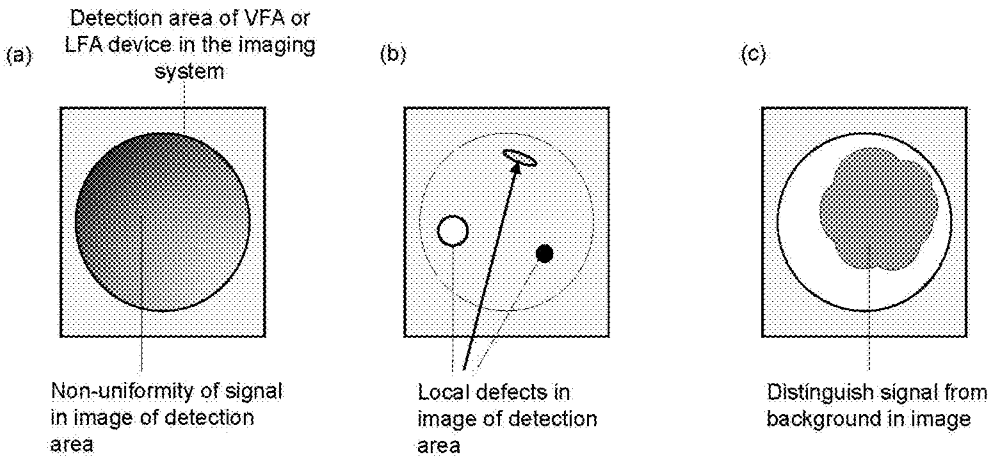
FIG. 4 shows three examples of detection of features in the analyte reaction area: (a) recognition of a non-uniform signal (e.g., color, intensity, darkness, particle distribution) in the image of the detection area; (b) detection of local defects in the detection area; and (c) detection of a boundary between signal and background areas in the image.

FIG. 4 shows examples of the detection of features in the detection area or analyte reaction area: (a) recognition of non-uniform signal (e.g., color/intensity/darkness/particle distribution) in the image of the detection area; (b) detection of local defects in the detection area; and (c) detection of the boundary of a signal and a background area in the image.

In some embodiment, the imaging software can distinguish and correct non-uniform signal distribution in the detection area. The signal average, median, standard deviation, and distribution slope can be used in the true signal analysis.

In some embodiment, the imaging software can distinguish and correct local defects in image of the detection area, such as air bubbles, local particle aggregation, unexpected color, non-uniformity in the manufactured device, and similar considerations. The imaging software can remove defects from the final signal.

In some embodiment, the imaging software can distinguish and correct signals or signal boundaries from a background image.

In some embodiment, the boundary of signal area detects background and has a width of 5 um, 10 um, 20 um, 50 um, 100 um, 200 um, 500 um, 1 mm, or an intermediate value or range.

In some embodiment, the signal in the detection area can be analyzed using red, green, blue, hue, saturation, brightness, grey channel, or a combination thereof.

Figure 8:
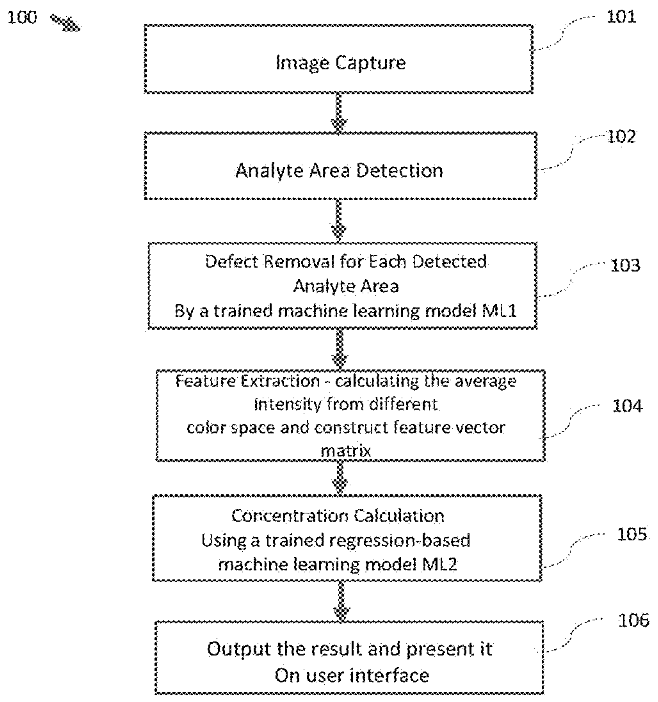
FIG. 8 shows an example of a software assay procedure from the initial image capture to final assay result based on machine learning from the assay detection area, including defect detection and removal, to the calculation of an analyte concentration.

FIG. 8 is an example of using software in the assay imaging and analysis procedure (100) from the initial image capture (101) to a final assay result based on machine learning from the assay detection area (102), defect detection and removal (103), feature extraction (104), to the calculation of analyte concentration (104), and finally presenting or displaying results of the procedure (106).

Figure 9:
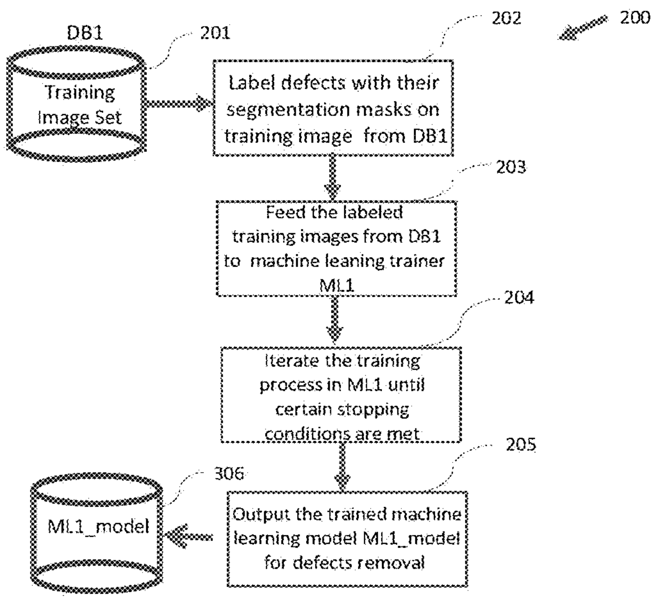
FIG. 9 shows an example of the training procedure of a machine learning model (200) for defects removal from a training image set including: providing the training an image set (201), detecting and labeling image defects in the training image set (202), feeding the labeled training images from DB1 to a machine learning trainer (203), iterating the training process in machine learning ML1 until certain stop conditions are met (204), outputting defects removal results of the trained machine learning model ML1_model (205), and storing in the ML1_model (306).

FIG. 9 is an example of training procedures of a machine learning that is dedicated to defect detection and removal from a set of training images.

In some embodiment, the system consists of 3 detection areas for 3 analytes; each detection area has a size of 2 mm to 5 mm; the imager has the field of view 20 mm by 20 mm with a resolution 2 um to 5 um. There are scale marker with a length 100 um to 500 um, a round shape marker and a color marker array within the FOV of imager and near the detection area.

In some embodiment, the system consists of 4 detection areas for 4 analytes; each detection area has a size of 1 mm to 2 mm; the imager has the field of view 5 mm by 4 mm with a resolution 1 um to 2 um. There are scale marker with a length 40 um to 100 um, square shape marker array with period 100 um to 200 um within the FOV of imager and within the detection area.

In some embodiment, the system consists of 1 detection areas for 1 analytes; each detection area has a size of 5 mm to 4 mm; the imager has the field of view 10 mm by 8 mm with a resolution 2 um to 4 um. There are scale marker with a length 1 mm to 5 mm, square shape marker array with period 100 um to 200 um within the FOV of imager and within the detection area.

In some embodiment, the system consists of 9 detection areas for 9 analytes; each detection area has a size of 0.5 mm to 1 mm; the imager has the field of view 10 mm by 10 mm with a resolution 1 um to 5 um. There are scale marker with a length 10 um to 100 um, round shape and color marker array with period 100 um to 200 um within the FOV of imager and within the detection area.

Example 1

Image Based Vertical Flow Assay and Lateral Flow Assay (LFA) Having a Reference

Figure 5:
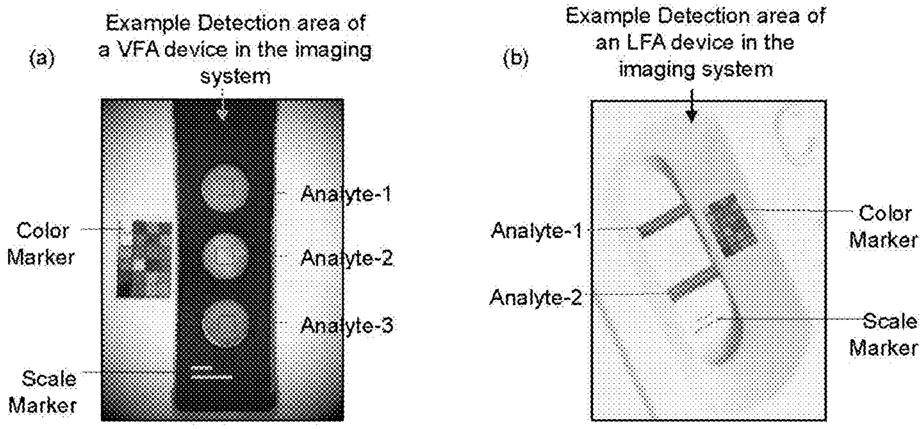
FIG. 5 shows examples of the detection area of a VFA or LFA device in the imaging system: (a) the detection area of a VFA device having three analyte detection areas, and a color marker and a scale marker as references; and (b) the detection area of an LFA device having two analyte detection areas, and a color marker and a scale marker as references.

FIG. 5 shows examples of the detection area of a VFA/LFA device in the imaging system: (a) the detection area of a VFA device having three analyte detection areas, and a color marker and a scale marker as references; and (b) the detection area of an LFA device having two analyte detection areas, and a color marker and a scale marker as references.

The (a) VFA example is detecting a Lipid Panel analyte including 3 analytes: total cholesterol; high density lipoprotein cholesterol (HDL cholesterol); and triglyceride concentration in blood using an imaging based vertical flow assay with reference to a color marker having 24 reference colors and a scale marker. The image is taken by a smartphone camera attached to a lens with a FoV of 25 mm×20 mm. The color is not uniform distributed in each area. Before analyzing the analytes, the image is corrected with size marker and color markers. The imperfection in each analyte area are removed.

The (b) LFA example is detecting 2 analytes in urine using an imaging based LFA with reference to a color marker including 24 reference colors and a scale marker. The color is not uniform distributed in both detection area and reference area. Before analyzing the analytes, the image is corrected with size marker and color markers. The imperfection in each analyte area are removed.

Example 2

Lipid Panel analyte detection using an image based vertical flow assay (VFA) with a reference. A device and a method of detecting a Lipid Panel analyte including total cholesterol, high density lipoprotein cholesterol (HDL cholesterol), and the triglyceride concentration in blood can use an imaging based vertical flow assay with a reference. The principle of the device and method is measuring the color of the detection area with a color reference to determine the cholesterol concentration in the blood samples. The detection area is imaged, compared to a reference, and error corrected with software.

Materials:

1. Fresh finger prick of blood or whole blood and collected in K2EDTA/heparin tubes.
2. A vertical flow assay strip with 3 detection areas presenting and detecting the Lipid Panel.
3. An imaging system having, for example, an iPhone camera, an external lens, and a light source with an optical fiber.

Method:

1. Drop 20 μL to 40 μL whole blood onto the vertical flow assay strip.
2. Insert the strip into the image capturing device.
3. The detecting device starts to capture images with a constant time interval.
4. The software recognizes the detection area of the assay from the image of the sample taken by the imager.
5. The software detects the overall reaction status based on color change and signal boundary.
6. The software detects local defects in the detected area for assaying, such as air bubbles, local particle aggregations, dust, and unexpected color. Then the software removes the defective areas in the sample for assay comprising: training a machine learning model, as depicted in FIG. 9, from the labeled images of defects to detect the defects in the areas for assaying with their segmentation masks that covers them in the image of the sample; based on the machine learning detection of (a), identifying the total area of detected defects and removing them from the image of the sample; and determining the exact area and volume of the remaining sample after the defect removal of (b) for subsequent assaying, utilizing the structure of the sample holding device.
7. The software further extracts the features from the image for assaying, such as the average intensity values of each channel from a different color space, including RGB, HSV, and Gray.
8. The software detects whether the remaining image has a non-uniform color development. If so, the software uses an algorithm to select and even out (i.e., smooth-out) the area.

9. Based on the processed image and the marker placed near the detection area, the software calculates the matrix of intensity feature values and constructs a feature vector matrix, from which a regression-based machine learning model is built to predict the concentration from the input feature vector matrix.
10. In assaying, the software determines the analyte concentration based on the regression-based machine learning model and presents the result on the user interface of the image capturing device.

Figure 6:
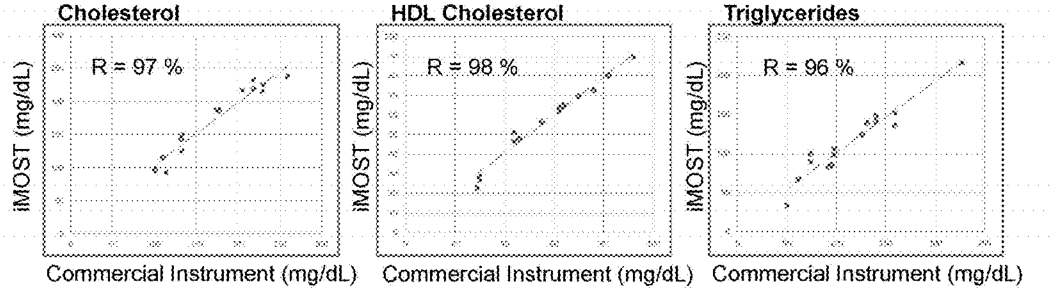
FIG. 6 shows example performance of a VFA device system detecting three analytes: cholesterol; high density lipoprotein cholesterol (HDL cholesterol); and triglyceride.
Figure 7:
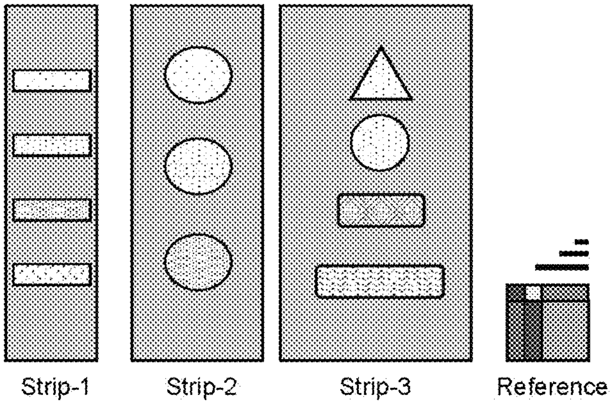
FIG. 7 shows an example of multiple test strips (Strip-1, Strip-2, and Strip-3) and at least one reference across one field-of-view (FoV) window in a field-of-view imaging system.

Result:

1. Cholesterol and triglyceride can react with enzymes coated on the strip and further generate a chromogen that absorbs red light and reflects blue light.
2. Light absorption of the detection area is determined by the software. The cholesterol and triglyceride concentration is positively correlated with the light absorption. Therefore, the blood cholesterol and triglyceride concentration can be determined.
3. FIG. 6 shows example performance of a VFA device system used to detect three analytes: cholesterol; high density lipoprotein cholesterol (HDL cholesterol); and triglyceride. With 11 tested cholesterol samples ranging from 102 mg/dL to 270 mg/dL, the system has an average error of 6.6%, R=97%. With 11 tested HDL cholesterol ranging from 28 mg/dL to 94 mg/dL, the system has an average error of 5.8%, R=98%. With 11 tested triglyceride samples ranging from 50 mg/dL to 230 mg/dL, the system has an average error of 10%, R=96%. Other instruments that can be used are "Essenlix iMOST" and the Commercial Instrument* was Cardiochek P-A from Poluymer Technolgies, Inc.

QMAX System

A) QMAX Card

Details of the QMAX card are described in detail in a variety of publications including International Application No. PCT/US2016/046437 (Essenlix Docket No. ESSN-028WO), which is hereby incorporated by reference herein for all purposes.

I. Plates

In present invention, generally, the plates of CROF are made of any material that (i) is capable of being used to regulate, together with the spacers, the thickness of a portion or entire volume of the sample, and (ii) has no significant adverse effects to a sample, an assay, or a goal that the plates intend to accomplish. However, in certain embodiments, particular materials (hence their properties) ae used for the plate to achieve certain objectives.

In certain embodiments, the two plates have the same or different parameters for each of the following parameters: plate material, plate thickness, plate shape, plate area, plate flexibility, plate surface property, and plate optical transparency.

(i) Plate Materials. The plates are made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1: The inorganic materials for the plates include, not limited to, glass, quartz, oxides, silicon-dioxide, silicon-nitride, hafnium oxide (HfO), aluminum oxide (AIO), semiconductors: (silicon, GaAs, GaN, etc.), metals (e.g. gold, silver, coper, aluminum, Ti, Ni, etc.), ceramics, or any combinations of thereof.

Mat-2: The organic materials for the spacers include, not limited to, polymers (e.g. plastics) or amorphous organic materials. The polymer materials for the spacers include, not limited to, acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In certain embodiments, the plates are each independently made of at least one of glass, plastic, ceramic, and metal. In certain embodiments, each plate independently includes at least one of glass, plastic, ceramic, and metal.

In certain embodiments, one plate is different from the other plate in lateral area, thickness, shape, materials, or surface treatment. In certain embodiments, one plate is the same as the other plate in lateral area, thickness, shape, materials, or surface treatment.

The materials for the plates are rigid, flexible or any flexibility between the two. The rigid (e.g. stiff) or flexibility is relative to a give pressing forces used in bringing the plates into the closed configuration.

In certain embodiments, a selection of rigid or flexible plate are determined from the requirements of controlling a uniformity of the sample thickness at the closed configuration.

In certain embodiments, at least one of the two plates are transparent (to a light). In certain embodiments at least a part or several parts of one plate or both plates are transparent. In certain embodiments, the plates are non-transparent.

(ii) Plate Thickness. In certain embodiments, the average thicknesses for at least one of the pates are 2 nm or less, 10 nm or less, 100 nm or less, 500 nm or less, 1000 nm or less, 2 um (micron) or less, 5 um or less, 10 um or less, 20 um or less, 50 um or less, 100 um or less, 150 um or less, 200 um or less, 300 um or less, 500 um or less, 800 um or less, 1 mm (millimeter) or less, 2 mm or less, 3 mm or less, or a range between any two of the values.

In certain embodiments, the average thicknesses for at least one of the plates are at most 3 mm (millimeter), at most 5 mm, at most 10 mm, at most 20 mm, at most 50 mm, at most 100 mm, at most 500 mm, or a range between any two of the values.

In certain embodiments, the thickness of a plate is not uniform across the plate. Using a different plate thickness at different location can be used to control the plate bending, folding, sample thickness regulation, and others.

(iii) Plate Shape and Area. Generally, the plates can have any shapes, as long as the shape allows a compress open flow of the sample and the regulation of the sample thickness. However, in certain embodiments, a particular shape can be advantageous. The shape of the plate can be round, elliptical, rectangles, triangles, polygons, ring-shaped, or any superpositions of these shapes.

In certain embodiments, the two plates can have the same size or shape, or different. The area of the plates depend on the application. The area of the plate is at most 1 mm2 (millimeter square), at most 10 mm2, at most 100 mm2, at most 1 cm2 (centimeter square), at most 5 cm2, at most 10 cm2, at most 100 cm2, at most 500 cm2, at most 1000 cm2, at most 5000 cm2, at most 10,000 cm2, or over 10,000 cm2, or any arrange between any of the two values. The shape of the plate can be rectangle, square, round, or others.

In certain embodiments, at least one of the plates is in the form of a belt (or strip) that has a width, thickness, and length. The width is at most 0.1 cm (centimeter), at most 0.5 cm, at most 1 cm, at most 5 cm, at most 10 cm, at most 50 cm, at most 100 cm, at most 500 cm, at most 1000 cm, or a range between any two of the values. The length can be as long it needed. The belt can be rolled into a roll.

(iv) Plate Surface Flatness. In many embodiments, an inner surface of the plates are flat or significantly flat, planar. In certain embodiments, the two inner surfaces are, at the closed configuration, parallel with each other. Flat inner surfaces facilitates a quantification and/or controlling of the sample thickness by simply using the predetermined spacer height at the closed configuration. For non-flat inner surfaces of the plate, one need to know not only the spacer height, but also the exact the topology of the inner surface to quantify and/or control the sample thickness at the closed configuration. To know the surface topology needs additional measurements and/or corrections, which can be complex, time consuming, and costly.

A flatness of the plate surface is relative to the final sample thickness (the final thickness is the thickness at the closed configuration), and is often characterized by the term of "relative surface flatness" is the ratio of the plate surface flatness variation to the final sample thickness.

In certain embodiments, the relative surface is less than 0.01%, 0.1%, less than 0.5%, less than 1%, less than 2%, less than 5%, less than 10%, less than 20%, less than 30%, less than 50%, less than 70%, less than 80%, less than 100%, or a range between any two of these values.

(v) Plate Surface Parallelness. In certain embodiments, the two surfaces of the plate is significantly parallel with each other. In certain embodiments, the two surfaces of the plate is not parallel with each other.

(vi) Plate Flexibility. In certain embodiments, a plate is flexible under the compressing of a CROF process. In certain embodiments, both plates are flexible under the compressing of a CROF process. In certain embodiments, a plate is rigid and another plate is flexible under the compressing of a CROF process. In certain embodiments, both plates are rigid. In certain embodiments, both plate are flexible but have different flexibility.

(vii) Plate Optical Transparency. In certain embodiments, a plate is optical transparent. In certain embodiments, both plates are optical transparent. In certain embodiments, a plate is optical transparent and another plate is opaque. In certain embodiments, both plates are opaque. In certain embodiments, both plate are optical transparent but have different optical transparency. The optical transparency of a plate can refer to a part or the entire area of the plate.

(viii) Surface Wetting Properties. In certain embodiments, a plate has an inner surface that wets (e.g. contact angle is less 90 degree) the sample, the transfer liquid, or both. In certain embodiments, both plates have an inner surface that wets the sample, the transfer liquid, or both; either with the same or different wettability. In certain embodiments, a plate has an inner surface that wets the sample, the transfer liquid, or both; and another plate has an inner surface that does not wet (e.g. the contact angle equal to or larger than 90 degree). The wetting of a plate inner surface can refer to a part or the entire area of the plate.

In certain embodiments, the inner surface of the plate has other nano or microstructures to control a lateral flow of a sample during a CROF. The nano or microstructures include, but not limited to, channels, pumps, and others. Nano and microstructures are also used to control the wetting properties of an inner surface.

II. Spacers (i) Spacers' Function. In present invention, the spacers are configured to have one or any combinations of the following functions and properties: the spacers are configured to (1) control, together with the plates, the thickness of the sample or a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

(ii) Spacer Architectures and Shapes. To achieve desired sample thickness reduction and control, in certain embodiments, the spacers are fixed its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) is a single spacer or a plurality of spacers. (e.g. an array). Certain embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (e.g. the sample flows around and pass the spacer. For example, a post as the spacer), and the enclosed spacer is the spacer that stop the sample flow (e.g. the sample cannot flow beyond the spacer. For example, a ring shape spacer and the sample is inside the ring). Both types of spacers use their height to regular the final sample thickness at a closed configuration.

In certain embodiments, the spacers are open-spacers only. In certain embodiments, the spacers are enclosed-spacers only. In certain embodiments, the spacers are a combination of open-spacers and enclosed-spacers.

The term "pillar spacer" means that the spacer has a pillar shape and the pillar shape can refer to an object that has height and a lateral shape that allow a sample to flow around it during a compressed open flow.

In certain embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0 1, 2, 3, 4, . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In certain embodiments, the spacers can be and/or can include posts, columns, beads, spheres, and/or other suitable geometries. The lateral shape and dimension (e.g., transverse to the respective plate surface) of the spacers can be anything, except, in certain embodiments, the following restrictions: (i) the spacer geometry will not cause a significant error in measuring the sample thickness and volume; or (ii) the spacer geometry would not prevent the out-flowing of the sample between the plates (e.g. it is not in enclosed form). But in certain embodiments, they require some spacers to be closed spacers to restrict the sample flow.

In certain embodiments, the shapes of the spacers have rounded corners. For example, a rectangle shaped spacer has one, several or all corners rounded (like a circle rather 90 degree angle). A round corner often make a fabrication of the spacer easier, and in some cases less damage to a biological material.

The sidewall of the pillars can be straight, curved, sloped, or different shaped in different section of the sidewall. In certain embodiments, the spacers are pillars of various lateral shapes, sidewalls, and pillar-height to pillar lateral area ratio. In a preferred embodiment, the spacers have shapes of pillars for allowing open flow.

(iii) Spacers' Materials. In the present invention, the spacers are generally made of any material that is capable of being used to regulate, together with the two plates, the thickness of a relevant volume of the sample. In certain embodiments, the materials for the spacers are different from that for the plates. In certain embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

(iv) Spacers' Mechanical Strength and Flexibility. In certain embodiments, the mechanical strength of the spacers are strong enough, so that during the compression and at the closed configuration of the plates, the height of the spacers is the same or significantly same as that when the plates are in an open configuration. In certain embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

(v) Spacers Inside Sample. To achieve desired sample thickness reduction and control, particularly to achieve a good sample thickness uniformity, in certain embodiments, the spacers are placed inside the sample, or the relevant volume of the sample. In certain embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" can be determined by a sample thickness uniformity or a required sample flow property during a CROF.

(vi) Spacer Height. In certain embodiments, all spacers have the same pre-determined height. In certain embodiments, spacers have different pre-determined height. In certain embodiments, spacers can be divided into groups or regions, wherein each group or region has its own spacer height. And in certain embodiments, the predetermined height of the spacers is an average height of the spacers. In certain embodiments, the spacers have approximately the same height. In certain embodiments, a percentage of number of the spacers have the same height.

The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 um or less, 2 um or less, 3 um or less, 5 um or less, 10 um or less, 20 um or less, 30 um or less, 50 um or less, 100 um or less, 150 um or less, 200 um or less, 300 um or less, 500 um or less, 800 um or less, 1 mm or less, 2 mm or less, 4 mm or less, or a range between any two of the values.

The spacer height and/or sample thickness is between 1 nm to 100 nm in one preferred embodiment, 100 nm to 500 nm in another preferred embodiment, 500 nm to 1000 nm in a separate preferred embodiment, 1 um (e.g. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment.

In certain embodiments, the spacer height and/or sample thickness (i) equal to or slightly larger than the minimum dimension of an analyte, or (ii) equal to or slightly larger than the maximum dimension of an analyte. The "slightly larger" means that it is about 1% to 5% larger and any number between the two values.

In certain embodiments, the spacer height and/or sample thickness is larger than the minimum dimension of an analyte (e.g. an analyte has an anisotropic shape), but less than the maximum dimension of the analyte.

For example, the red blood cell has a disk shape with a minim dimension of 2 um (disk thickness) and a maximum dimension of 11 um (a disk diameter). In an embodiment of the present invention, the spacers is selected to make the inner surface spacing of the plates in a relevant area to be 2 um (equal to the minimum dimension) in one embodiment, 2.2 um in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 um and any number between the two values, a undiluted whole blood sample is confined in the spacing, on average, each red blood cell (RBC) does not overlap with others, allowing an accurate counting of the red blood cells visually. (Too many overlaps between the RBC's can cause serious errors in counting).

In the present invention, in certain embodiments, it uses the plates and the spacers to regulate not only a thickness of a sample, but also the orientation and/or surface density of the analytes/entity in the sample when the plates are at the closed configuration. When the plates are at a closed configuration, a thinner thickness of the sample gives a less the analytes/entity per surface area (e.g. less surface concentration).

(vii) Spacer Lateral Dimension. For an open-spacer, the lateral dimensions can be characterized by its lateral dimension (sometime being called width) in the x and y—two orthogonal directions. The lateral dimension of a spacer in each direction is the same or different. In certain embodiments, the lateral dimension for each direction (x or y) is . . . .

In certain embodiments, the ratio of the lateral dimensions of x toy direction is 1, 1.5, 2, 5, 10, 100, 500, 1000, 10,000, or a range between any two of the value. In certain embodiments, a different ratio is used to regulate the sample flow direction; the larger the ratio, the flow is along one direction (larger size direction).

In certain embodiments, the different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height.

In certain embodiments, all spacers have the same shape and dimensions. In certain embodiments, each of the spacers have different lateral dimensions.

For enclosed-spacers, in certain embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

(viii) Aspect Ratio of Height to the Average Lateral Dimension of Pillar Spacer. In certain embodiments, the aspect ratio of the height to the average lateral dimension of the pillar spacer is 100,000, 10,000, 1,000, 100, 10, 1, 0.1, 0.01, 0.001, 0.0001, 0, 00001, or a range between any two of the values.

(ix) Spacer Height Precisions. The spacer height should be controlled precisely. The relative precision of the spacer (e.g. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

(x) Inter-Spacer Distance. The spacers can be a single spacer or a plurality of spacers on the plate or in a relevant area of the sample. In certain embodiments, the spacers on the plates are configured and/or arranged in an array form, and the array is a periodic, non-periodic array or periodic in some locations of the plate while non-periodic in other locations.

In certain embodiments, the periodic array of the spacers has a lattice of square, rectangle, triangle, hexagon, polygon, or any combinations of thereof, where a combination means that different locations of a plate has different spacer lattices.

In certain embodiments, the inter-spacer distance of a spacer array is periodic (e.g. uniform inter-spacer distance) in at least one direction of the array. In certain embodiments, the inter-spacer distance is configured to improve the uniformity between the plate spacing at a closed configuration.

The distance between neighboring spacers (e.g. the inter-spacer distance) is 1 um or less, 5 um or less, 10 um or less, 20 um or less, 30 um or less, 40 um or less, 50 um or less, 60 um or less, 70 um or less, 80 um or less, 90 um or less, 100 um or less, 200 um or less, 300 um or less, 400 um or less, or a range between any two of the values.

In certain embodiments, the inter-spacer distance is at 400 or less, 500 or less, 1 mm or less, 2 mm or less, 3 mm or less, 5 mm or less, 7 mm or less, 10 mm or less, or any range between the values. In certain embodiments, the inter-spacer distance is a 10 mm or less, 20 mm or less, 30 mm or less, 50 mm or less, 70 mm or less, 100 mm or less, or any range between the values.

The distance between neighboring spacers (e.g. the inter-spacer distance) is selected so that for a given properties of the plates and a sample, at the closed-configuration of the plates, the sample thickness variation between two neighboring spacers is, in certain embodiments, at most 0.5%, 1%, 5%, 10%, 20%, 30%, 50%, 80%, or any range between the values; or in certain embodiments, at most 80%, 100%, 200%, 400%, or a range between any two of the values.

Clearly, for maintaining a given sample thickness variation between two neighboring spacers, when a more flexible plate is used, a closer inter-spacer distance is needed.

Specify the accuracy of the inter spacer distance.

In a preferred embodiment, the spacer is a periodic square array, wherein the spacer is a pillar that has a height of 2 to 4 um, an average lateral dimension of from 5 to 20 um, and inter-spacer spacing of 1 um to 100 um.

In a preferred embodiment, the spacer is a periodic square array, wherein the spacer is a pillar that has a height of 2 to 4 um, an average lateral dimension of from 5 to 20 um, and inter-spacer spacing of 100 um to 250 um.

In a preferred embodiment, the spacer is a periodic square array, wherein the spacer is a pillar that has a height of 4 to 50 um, an average lateral dimension of from 5 to 20 um, and inter-spacer spacing of 1 um to 100 um.

In a preferred embodiment, the spacer is a periodic square array, wherein the spacer is a pillar that has a height of 4 to 50 um, an average lateral dimension of from 5 to 20 um, and inter-spacer spacing of 100 um to 250 um.

The period of spacer array is between 1 nm to 100 nm in one preferred embodiment, 100 nm to 500 nm in another preferred embodiment, 500 nm to 1000 nm in a separate preferred embodiment, 1 um (e.g. 1000 nm) to 2 um in another preferred embodiment, 2 um to 3 um in a separate preferred embodiment, 3 um to 5 um in another preferred embodiment, 5 um to 10 um in a separate preferred embodiment, and 10 um to 50 um in another preferred embodiment, 50 um to 100 um in a separate preferred embodiment, 100 um to 175 um in a separate preferred embodiment, and 175 um to 300 um in a separate preferred embodiment.

(xi) Spacer Density. The spacers are arranged on the respective plates at a surface density of greater than one per $um^2$, greater than one per 10 $um^2$, greater than one per 100 $um^2$, greater than one per 500 $um^2$, greater than one per 1000 $um^2$, greater than one per 5000 $um^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or a range between any two of the values.

(3) the spacers are configured to not take significant surface area (volume) in a given sample area (volume);

(xii) Ratio of Spacer Volume to Sample Volume. In many embodiments, the ratio of the spacer volume (e.g. the volume of the spacer) to sample volume (e.g. the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (e.g. flow speed, flow direction, etc.).

In certain embodiments, the ratio of the spacer volume r) to sample volume, and/or the ratio of the volume of the spacers that are inside of the relevant volume of the sample to the relevant volume of the sample is less than 100%, at most 99%, at most 70%, at most 50%, at most 30%, at most 10%, at most 5%, at most 3% at most 1%, at most 0.1%, at most 0.01%, at most 0.001%, or a range between any of the values.

(xiii) Spacers Fixed to Plates. The inter spacer distance and the orientation of the spacers, which play a key role in the present invention, are preferably maintained during the process of bringing the plates from an open configuration to the closed configuration, and/or are preferably predetermined before the process from an open configuration to a closed configuration.

In certain embodiments of the present disclosure, spacers are fixed on one of the plates before bring the plates to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (e.g. the spacer moves away from its original position on the plate surface).

In certain embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In certain embodiments, a spacer is fixed to a plate monolithically.

In certain embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (e.g. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

In certain embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In certain embodiments, at least a distance between two spacers is predetermined ("predetermined inter-spacer distance" means that the distance is known when a user uses the plates).

In certain embodiments of all methods and devices described herein, there are additional spacers besides to the fixed spacers.

(xiv) Specific Sample Thickness. In present invention, it was observed that a larger plate holding force (e.g. the force that holds the two plates together) can be achieved by using a smaller plate spacing (for a given sample area), or a larger sample area (for a given plate-spacing), or both.

In certain embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

The spacers can be fabricated on a plate in a variety of ways, using lithography, etching, embossing (nanoimprint), depositions, lift-off, fusing, or a combination of thereof. In certain embodiments, the spacers are directly embossed or imprinted on the plates. In certain embodiments, the spacers imprinted into a material (e.g. plastics) that is deposited on the plates. In certain embodiments, the spacers are made by directly embossing a surface of a CROF plate. The nanoimprinting can be done by roll to roll technology using a roller imprinter, or roll to a planar nanoimprint. Such process has a great economic advantage and hence lowering the cost.

In certain embodiments, the spacers are deposited on the plates. The deposition can be evaporation, pasting, or a lift-off. In the pasting, the spacer is fabricated first on a carrier, then the spacer is transferred from the carrier to the plate. In the lift-off, a removable material is first deposited on the plate and holes are created in the material; the hole bottom expose the plate surface and then a spacer material is deposited into the hole and afterwards the removable material is removed, leaving only the spacers on the plate surface. In certain embodiments, the spacers deposited on the plate are fused with the plate. In certain embodiments, the spacer and the plates are fabricated in a single process. The single process includes imprinting (e.g. embossing, molding) or synthesis.

In certain embodiments, at least two of the spacers are fixed to the respective plate by different fabrication methods, and optionally wherein the different fabrication methods include at least one of being deposition, bonded, fuse, imprinted, and etched.

In certain embodiments, one or more of the spacers are fixed to the respective plate(s) is by a fabrication method of being bonded, being fused, being imprinted, or being etched, or any combination of thereof.

In certain embodiments, the fabrication methods for forming such monolithic spacers on the plate include a method of being bonded, being fused, being imprinted, or being etched, or any combination of thereof.

B) Adaptor

Details of the Adaptor are described in detail in a variety of publications including International Application No.

PCT/US2018/017504 (Essenlix Docket No. ESXPCT18F04), which is hereby incorporated by reference herein for all purposes.

The present invention that is described herein address this problem by providing a system comprising an optical adaptor and a smartphone. The optical adaptor device fits over a smartphone converting it into a microscope which can take both fluorescent and bright-field images of a sample. This system can be operated conveniently and reliably by a common person at any location. The optical adaptor takes advantage of the existing resources of the smartphone, including camera, light source, processor and display screen, which provides a low-cost solution let the user to do bright-field and fluorescent microscopy.

In this invention, the optical adaptor device comprises a holder frame fitting over the upper part of the smartphone and an optical box attached to the holder having sample receptacle slot and illumination optics. In some references (U.S. Pat. No. 2016/029091 and U.S. Pat. No. 2011/0292198), their optical adaptor design is a whole piece including both the clip-on mechanics parts to fit over the smartphone and the functional optics elements. This design has the problem that they need to redesign the whole-piece optical adaptor for each specific model of smartphone. But in this present invention, the optical adaptor is separated into a holder frame only for fitting a smartphone and a universal optical box containing all the functional parts. For the smartphones with different dimensions, as long as the relative positions of the camera and the light source are the same, only the holder frame need to be redesigned, which will save a lot of cost of design and manufacture.

The optical box of the optical adaptor comprises: a receptacle slot which receives and position the sample in a sample slide in the field of view and focal range of the smartphone camera; a bright-field illumination optics for capturing bright-field microscopy images of a sample; a fluorescent illumination optics for capturing fluorescent microscopy images of a sample; a lever to switch between bright-field illumination optics and fluorescent illumination optics by sliding inward and outward in the optical box.

The receptacle slot has a rubber door attached to it, which can fully cover the slot to prevent the ambient light getting into the optical box to be collected by the camera. In U.S. Pat. 2016/0290916, the sample slot is always exposed to the ambient light which won't cause too much problem because it only does bright-field microscopy. But the present invention can take the advantage of this rubber door when doing fluorescent microscopy because the ambient light would bring a lot of noise to the image sensor of the camera.

To capture good fluorescent microscopy image, it is desirable that nearly no excitation light goes into the camera and only the fluorescent emitted by the sample is collected by the camera. For all common smartphones, however, the optical filter putting in front of the camera cannot block the undesired wavelength range of the light emitted from the light source of a smartphone very well due to the large divergence angle of the beams emitted by the light source and the optical filter not working well for un-collimated beams. Collimation optics can be designed to collimated the beam emitted by the smartphone light source to address this issue, but this approach increase the size and cost of the adaptor. Instead, in this present invention, fluorescent illumination optics enables the excitation light to illuminate the sample partially from the waveguide inside the sample slide and partially from the backside of the sample side in large oblique incidence angle so that excitation light will nearly not be collected by the camera to reduce the noise signal getting into the camera.

The bright-field illumination optics in the adaptor receive and turn the beam emitted by the light source so as to back-illuminated the sample in normal incidence angle.

Typically, the optical box also comprises a lens mounted in it aligned with the camera of the smartphone, which magnifies the images captured by the camera. The images captured by the camera can be further processed by the processor of smartphone and outputs the analysis result on the screen of smartphone.

To achieve both bright-field illumination and fluorescent illumination optics in a same optical adaptor, in this present invention, a slidable lever is used. The optical elements of the fluorescent illumination optics are mounted on the lever and when the lever fully slides into the optical box, the fluorescent illumination optics elements block the optical path of bright-field illumination optics and switch the illumination optics to fluorescent illumination optics. And when the lever slides out, the fluorescent illumination optics elements mounted on the lever move out of the optical path and switch the illumination optics to bright-field illumination optics. This lever design makes the optical adaptor work in both bright-field and fluorescent illumination modes without the need for designing two different single-mode optical boxes.

The lever comprises two planes at different planes at different heights.

In certain embodiments, two planes can be joined together with a vertical bar and move together in or out of the optical box. In certain embodiments, two planes can be separated and each plane can move individually in or out of the optical box.

The upper lever plane comprises at least one optical element which can be, but not limited to be an optical filter. The upper lever plane moves under the light source and the preferred distance between the upper lever plane and the light source is in the range of 0 to 5 mm.

Part of the bottom lever plane is not parallel to the image plane. And the surface of the non-parallel part of the bottom lever plane has mirror finish with high reflectivity larger than 95%. The non-parallel part of the bottom lever plane moves under the light source and deflects the light emitted from the light source to back-illuminate the sample area right under the camera. The preferred tilt angle of the non-parallel part of the bottom lever plane is in the range of 45 degree to 65 degree and the tilt angle is defined as the angle between the non-parallel bottom plane and the vertical plane.

Part of the bottom lever plane is parallel to the image plane and is located under and 1 mm to 10 mm away from the sample. The surface of the parallel part of the bottom lever plane is highly light absorptive with light absorption larger than 95%. This absorptive surface is to eliminate the reflective light back-illuminating on the sample in small incidence angle.

To slide in and out to switch the illumination optics using the lever, a stopper design comprising a ball plunger and a groove on the lever is used in order to stop the lever at a pre-defined position when being pulled outward from the adaptor. This allow the user to use arbitrary force the pull the lever but make the lever to stop at a fixed position where the optical adaptor's working mode is switched to bright-filed illumination.

A sample slider is mounted inside the receptacle slot to receive the QMAX device and position the sample in the QMAX device in the field of view and focal range of the smartphone camera.

The sample slider comprises a fixed track frame and a moveable arm:

The frame track is fixedly mounted in the receptacle slot of the optical box. And the track frame has a sliding track slot that fits the width and thickness of the QMAX device so that the QMAX device can slide along the track. The width and height of the track slot is carefully configured to make the QMAX device shift less than 0.5 mm in the direction perpendicular to the sliding direction in the sliding plane and shift less than less than 0.2 mm along the thickness direction of the QMAX device.

The frame track has an opened window under the field of view of the camera of smartphone to allow the light back-illuminate the sample.

A moveable arm is pre-built in the sliding track slot of the track frame and moves together with the QMAX device to guide the movement of QMAX device in the track frame.

The moveable arm equipped with a stopping mechanism with two pre-defined stop positions. For one position, the arm will make the QMAX device stop at the position where a fixed sample area on the QMAX device is right under the camera of smartphone. For the other position, the arm will make the QMAX device stop at the position where the sample area on QMAX device is out of the field of view of the smartphone and the QMAX device can be easily taken out of the track slot.

The moveable arm switches between the two stop positions by a pressing the QMAX device and the moveable arm together to the end of the track slot and then releasing.

The moveable arm can indicate if the QMAX device is inserted in correct direction. The shape of one corner of the QMAX device is configured to be different from the other three right angle corners. And the shape of the moveable arm matches the shape of the corner with the special shape so that only in correct direction can QMAX device slide to correct position in the track slot.

C) Smartphone/Detection System

Details of the Smartphone/Detection System are described in detail in a variety of publications including International Application (IA) No. PCT/US2016/046437 filed on Aug. 10, 2016, IA No. PCT/US2016/051775 filed Sep. 14, 2016, U.S. Provisional Application No. 62/456,065, which was filed on Feb. 7, 2017, U.S. Provisional Application Nos. 62/456,287 and 62/456,590, which were filed on Feb. 8, 2017, U.S. Provisional Application No. 62/456,504, which was filed on Feb. 8, 2017, U.S. Provisional Application No. 62/459,544, which was filed on Feb. 15, 2017, and U.S. Provisional Application Nos. 62/460,075 and 62/459,920, which were filed on Feb. 16, 2017, each of which are hereby incorporated herein by reference in their entirety for all purposes.

The devices/apparatus, systems, and methods herein disclosed can include or use Q-cards for sample detection, analysis, and quantification. In certain embodiments, the Q-card is used together with an adaptor that can connect the Q-card with a smartphone detection system. In certain embodiments, the smartphone comprises a camera and/or an illumination source. In certain embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In certain embodiments, the smartphone comprises a camera, but the camera is not used for image capturing.

In certain embodiments, the smartphone comprises a light source such as but not limited to LED (light emitting diode). In certain embodiments, the light source is used to provide illumination to the sample when the sample is positioned in the field of view of the camera (e.g. by an adaptor). In certain embodiments, the light from the light source is enhanced, magnified, altered, and/or optimized by optical components of the adaptor.

In certain embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In certain embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In certain embodiments, the smartphone is an iPhone™, an Android™ phone, or a Windows™ phone.

D) Method of Manufacture

Details of the Method of Manufacture are described in detail in a variety of publications including International Application No. PCT/US2018/057873 filed Oct. 26, 2018, which is hereby incorporated by reference herein for all purposes.

Devices of the disclosure can be fabricated using techniques well known in the art. The choice of fabrication technique will depend on the material used for the device and the size of the spacer array and/or the size of the spacers. Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC), and combinations thereof. Other materials are known in the art. For example, deep Reactive Ion Etch (DRIE) is used to fabricate silicon-based devices with small gaps, small spacers and large aspect ratios (ratio of spacer height to lateral dimension). Thermoforming (embossing, injection molding) of plastic devices can also be used, e.g., when the smallest lateral feature is >20 microns and the aspect ratio of these features is ≤10.

Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) can be employed. Techniques such as laser micromachining can be adopted for plastic materials with high photon absorption efficiency. This technique is suitable for lower throughput fabrication because of the serial nature of the process. For mass-produced plastic devices, thermoplastic injection molding, and compression molding can be suitable. Conventional thermoplastic injection molding used for mass-fabrication of compact discs (which preserves fidelity of features in sub-microns) can also be employed to fabricate the devices of the invention. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding can be chosen as the method of manufacture. Compression molding (also called hot embossing or relief imprinting) has the advantages of being compatible with high molecular weight polymers, which are excellent for small structures and can replicate high aspect ratio structures but has longer cycle times. Injection molding works well for low aspect ratio structures and is most suitable for low molecular weight polymers.

A device can be fabricated in one or more pieces that are then assembled. Layers of a device can be bonded together by clamps, adhesives, heat, anodic bonding, or reactions between surface groups (e.g., wafer bonding). Alternatively, a device with channels or gaps in more than one plane can be fabricated as a single piece, e.g., using stereolithography or other three-dimensional fabrication techniques.

To reduce non-specific adsorption of cells or compounds released by lysed cells onto the surfaces of the device, one or more surfaces of the device can be chemically modified to be non-adherent or repulsive. The surfaces can be coated with a thin film coating (e.g., a monolayer) of commercial non-stick reagents, such as those used to form hydrogels. Additional examples chemical species that can be used to modify the surfaces of the device include oligoethylene glycols, fluorinated polymers, organosilanes, thiols, polyethylene glycol, hyaluronic acid, bovine serum albumin, poly-vinyl alcohol, mucin, poly-HEMA, methacrylated PEG, and agarose. Charged polymers can also be employed to repel oppositely charged species. The type of chemical species used for repulsion and the method of attachment to the surfaces of the device will depend on the nature of the species being repelled and the nature of the surfaces and the species being attached. Such surface modification techniques are well known in the art. The surfaces can be functionalized before or after the device is assembled. The surfaces of the device can also be coated in order to capture materials in the sample, e.g., membrane fragments or proteins.

In certain embodiments of the present disclosure, a method for fabricating any Q-Card of the present disclosure can comprise injection molding of the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise Laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise injection molding and laser cutting the first plate. In certain embodiments of the present disclosure, a method for fabricating any Q-Card of the present disclosure can comprise nanoimprinting or extrusion printing of the second plate. In certain embodiments of the present disclosure, a method for fabricating any Q-Card of the present disclosure can comprise nanoimprinting or extrusion printing to fabricated both the first and the second plate. In certain embodiments of the present disclosure, a method for fabricating any Q-Card of the present disclosure can comprise fabricating the first plate or the second plate, using injection molding, laser cutting the first plate, nanoimprinting, extrusion printing, or a combination of thereof. In certain embodiments of the present disclosure, a method for fabricating any Q-Card of the present disclosure can comprise a step of attaching the hinge on the first and the second plates after the fabrication of the first and second plates.

E) Sample Types & Subjects

Details of the Samples & Subjects are described in detail in a variety of publications including International Application (IA) No. PCT/US2016/046437 filed on Aug. 10, 2016, IA No. PCT/US2016/051775 filed on Sep. 14, 2016, IA No. PCT/US201/017307 filed on Feb. 7, 2018, IA No. and PCT/US2017/065440 filed on Dec. 8, 2017, each of which is hereby incorporated by reference herein for all purposes.

A sample can be obtained from a subject. A subject as described herein can be of any age and can be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). A particular class of subjects that can benefit is subjects who have or are suspected of having an infection (e.g., a bacterial and/or a viral infection). Another particular class of subjects that can benefit is subjects who can be at higher risk of getting an infection. Furthermore, a subject treated by any of the methods or compositions described herein can be male or female. Any of the methods, devices, or kits disclosed herein can also be performed on a non-human subject, such as a laboratory or farm animal. Non-limiting examples of a non-human subjects include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

The devices, apparatus, systems, and methods herein disclosed can be used for samples such as but not limited to diagnostic samples, clinical samples, environmental samples and foodstuff samples.

For example, in certain embodiments, the devices, apparatus, systems, and methods herein disclosed are used for a sample that includes cells, tissues, bodily fluids and/or a mixture thereof. In certain embodiments, the sample comprises a human body fluid. In certain embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In certain embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In certain embodiments, the devices, apparatus, systems, and methods herein disclosed are used for a foodstuff sample, which is suitable or has the potential to become suitable for animal consumption, e.g., human consumption. In certain embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter (uL, also "uL" herein) or less, 500 μL or less, 300 uL or less, 250 uL or less, 200 uL or less, 170 uL or less, 150 uL or less, 125 uL or less, 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values.

In certain embodiments, the volume of the sample includes, but is not limited to, about 100 uL or less, 75 uL or less, 50 uL or less, 25 uL or less, 20 uL or less, 15 uL or less, 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values. In certain embodiments, the volume of the sample includes, but is not limited to, about 10 uL or less, 5 uL or less, 3 uL or less, 1 uL or less, 0.5 uL or less, 0.1 uL or less, 0.05 uL or less, 0.001 uL or less, 0.0005 uL or less, 0.0001 uL or less, 10 pL or less, 1 pL or less, or a range between any two of the values.

In certain embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

F) Machine Learning

Details of the Network are described in detail in a variety of publications including International Application (IA) No. PCT/US2018/017504 filed Feb. 8, 2018, and PCT/US2018/057877 filed Oct. 26, 2018, each of which are hereby incorporated by reference herein for all purposes.

One aspect of the present invention provides a framework of machine learning and deep learning for analyte detection and localization. A machine learning algorithm is an algorithm that is able to learn from data. A more rigorous definition of machine learning is "A computer program is said to learn from experience E with respect to some class of tasks T and performance measure P, if its performance at tasks in T, as measured by P, improves with experience E." It explores the study and construction of algorithms that can learn from and make predictions on data—such algorithms overcome the static program instructions by making data driven predictions or decisions, through building a model from sample inputs.

Deep learning is a specific kind of machine learning based on a set of algorithms that attempt to model high level abstractions in data. In a simple case, there might be two sets of neurons: ones that receive an input signal and ones that send an output signal. When the input layer receives an input, it passes on a modified version of the input to the next layer. In a deep network, there are many layers between the input and output (and the layers are not made of neurons but it can help to think of it that way), allowing the algorithm to use multiple processing layers, composed of multiple linear and non-linear transformations.

One aspect of the present invention is to provide two analyte detection and localization approaches. The first approach is a deep learning approach and the second approach is a combination of deep learning and computer vision approaches.

(i) Deep Learning Approach. In the first approach, the disclosed analyte detection and localization workflow consists of two stages, training and prediction. We describe training and prediction stages in the following paragraphs.

(a) Training Stage

In the training stage, training data with annotation is fed into a convolutional neural network. Convolutional neural network is a specialized neural network for processing data that has a grid-like, feed forward and layered network topology. Examples of the data include time-series data, which can be thought of as a 1D grid taking samples at regular time intervals, and image data, which can be thought of as a 2D grid of pixels. Convolutional networks have been successful in practical applications. The name "convolutional neural network" indicates that the network employs a mathematical operation called convolution. Convolution is a specialized kind of linear operation. Convolutional networks are simply neural networks that use convolution in place of general matrix multiplication in at least one of their layers.

The machine learning model receives one or multiple images of samples that contain the analytes taken by the imager over the sample holding QMAX device as training data. Training data are annotated for analytes to be assayed, wherein the annotations indicate whether or not analytes are in the training data and where they locate in the image. Annotation can be done in the form of tight bounding boxes which fully contains the analyte, or center locations of analytes. In the latter case, center locations are further converted into circles covering analytes or a Gaussian kernel in a point map.

When the size of training data is large, training machine learning model presents two challenges: annotation (usually done by human) is time consuming, and the training is computationally expensive. To overcome these challenges, one can partition the training data into patches of small size, then annotate and train on these patches, or a portion of these patches. The term "machine learning" can refer to algorithms, systems and apparatus in the field of artificial intelligence that often use statistical techniques and artificial neural network trained from data without being explicitly programmed.

The annotated images are fed to the machine learning (ML) training module, and the model trainer in the machine learning module will train a ML model from the training data (annotated sample images). The input data will be fed to the model trainer in multiple iterations until certain stopping criterion is satisfied. The output of the ML training module is a ML model—a computational model that is built from a training process in the machine learning from the data that gives computer the capability to perform certain tasks (e.g. detect and classify the objects) on its own.

The trained machine learning model is applied during the predication (or inference) stage by the computer. Examples of machine learning models include ResNet, DenseNet, etc. which are also named as "deep learning models" because of the depth of the connected layers in their network structure. In certain embodiments, the Caffe library with fully convolutional network (FCN) was used for model training and predication, and other convolutional neural network architecture and library can also be used, such as TensorFlow.

The training stage generates a model that will be used in the prediction stage. The model can be repeatedly used in the prediction stage for assaying the input. Thus, the computing unit only needs access to the generated model. It does not need access to the training data, nor requiring the training stage to be run again on the computing unit.

(b) Prediction Stage

In the predication/inference stage, a detection component is applied to the input image, and an input image is fed into the predication (inference) module preloaded with a trained model generated from the training stage. The output of the prediction stage can be bounding boxes that contain the detected analytes with their center locations or a point map indicating the location of each analyte, or a heatmap that contains the information of the detected analytes.

When the output of the prediction stage is a list of bounding boxes, the number of analytes in the image of the sample for assaying is characterized by the number of detected bounding boxes. When the output of the prediction stage is a point map, the number of analytes in the image of the sample for assaying is characterized by the integration of the point map. When the output of the prediction is a heatmap, a localization component is used to identify the location and the number of detected analytes is characterized by the entries of the heatmap.

One embodiment of the localization algorithm is to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list. In the detection component using heatmap, an input image, along with the model generated from the training stage, is fed into a convolutional neural network, and the output of the detection stage is a pixel-level prediction, in the form of a heatmap. The heatmap can have the same size as the input image, or it can be a scaled down version of the input image, and it is the input to the localization component. We disclose an algorithm to localize the analyte center. The main idea is to iteratively detect local peaks from the heatmap. After the peak is localized, we calculate the local area surrounding the peak but with smaller value. We remove this region from the heatmap and find the next peak from the remaining pixels. The process is repeated only all pixels are removed from the heatmap.

In certain embodiments, the present invention provides the localization algorithm to sort the heatmap values into a one-dimensional ordered list, from the highest value to the lowest value. Then pick the pixel with the highest value, remove the pixel from the list, along with its neighbors. Iterate the process to pick the pixel with the highest value in the list, until all pixels are removed from the list.

```
Algorithm GlobalSearch (heatmap)
Input:
    heatmap
Output:
    loci
loci ←{ }
sort(heatmap)
while (heatmap is not empty) {
  s ← pop(heatmap)
  D ← {disk center as s with radius R}
  heatmap = heatmap \ D // remove D from the heatmap
  add s to loci
}
```

After sorting, heatmap is a one-dimensional ordered list, where the heatmap value is ordered from the highest to the lowest. Each heatmap value is associated with its corresponding pixel coordinates. The first item in the heatmap is the one with the highest value, which is the output of the pop(heatmap) function. One disk is created, where the center is the pixel coordinate of the one with highest heatmap value. Then all heatmap values whose pixel coordinates resides inside the disk is removed from the heatmap. The algorithm repeatedly pops up the highest value in the current heatmap, removes the disk around it, till the items are removed from the heatmap.

In the ordered list heatmap, each item has the knowledge of the proceeding item, and the following item. When removing an item from the ordered list, we make the following changes:

Assume the removing item is $x_r$, its proceeding item is $x_p$, and its following item is $x_f$.

For the proceeding item $x_p$, re-define its following item to the following item of the removing item. Thus, the following item of $x_p$ is now $x_f$.

For the removing item $x_r$, un-define its proceeding item and following item, which removes it from the ordered list.

For the following item $x_r$, re-define its proceeding item to the proceeding item of the removed item. Thus, the proceeding item of $x_f$ is now $x_p$.

After all items are removed from the ordered list, the localization algorithm is complete. The number of elements in the set loci will be the count of analytes, and location information is the pixel coordinate for each s in the set loci.

Another embodiment searches local peak, which is not necessary the one with the highest heatmap value. To detect each local peak, we start from a random starting point, and search for the local maximal value. After we find the peak, we calculate the local area surrounding the peak but with smaller value. We remove this region from the heatmap and find the next peak from the remaining pixels. The process is repeated only all pixels are removed from the heatmap.

```
Algorithm LocalSearch (s, heatmap)
Input:
  s: starting location (x, y)
  heatmap
Output:
  s: location of local peak.
We only consider pixels of value > 0.
Algorithm Cover (s, heatmap)
Input:
  s: location of local peak.
  heatmap:
Output:
  cover: a set of pixels covered by peak:
```

This is a breadth-first-search algorithm starting from s, with one altered condition of visiting points: a neighbor p of the current location q is only added to cover if heatmap[p]>0 and heatmap[p]<=heatmap[q]. Therefore, each pixel in cover has a non-descending path leading to the local peak s.

```
Algorithm Localization (heatmap)
Input:
    heatmap
Output:
    loci
loci ←{ }
pixels ←{all pixels from heatmap}
while pixels is not empty {
  s ←any pixel from pixels
  s ←LocalSearch(s, heatmap)  // s is now local peak
  probe local region of radius R surrounding s for better local peak
  r ←Cover(s, heatmap)
  pixels ← pixels \ r           // remove all pixels in cover
  add s to loci
```

(ii) Mixture of Deep Learning and Computer Vision Approaches. In the second approach, the detection and localization are realized by computer vision algorithms, and a classification is realized by deep learning algorithms, wherein the computer vision algorithms detect and locate possible candidates of analytes, and the deep learning algorithm classifies each possible candidate as a true analyte and false analyte. The location of all true analyte (along with the total count of true analytes) will be recorded as the output.

(a) Detection. The computer vision algorithm detects possible candidate based on the characteristics of analytes, including but not limited to intensity, color, size, shape, distribution, etc. A pre-processing scheme can improve the detection. Pre-processing schemes include contrast enhancement, histogram adjustment, color enhancement, de-nosing, smoothing, de-focus, etc. After pre-processing, the input image is sent to a detector. The detector tells the existing of possible candidate of analyte and gives an estimate of its location. The detection can be based on the analyte structure (such as edge detection, line detection, circle detection, etc.), the connectivity (such as blob detection, connect components, contour detection, etc.), intensity, color, shape using schemes such as adaptive thresholding, etc.

(b) Localization. After detection, the computer vision algorithm locates each possible candidate of analytes by providing its boundary or a tight bounding box containing it. This can be achieved through object segmentation algorithms, such as adaptive thresholding, background subtraction, floodfill, mean shift, watershed, etc. Very often, the localization can be combined with detection to produce the detection results along with the location of each possible candidates of analytes.

(c) Classification. The deep learning algorithms, such as convolutional neural networks, achieve start-of-the-art visual classification. We employ deep learning algorithms for classification on each possible candidate of analytes. Various convolutional neural network can be utilized for analyte classification, such as VGGNet, ResNet, MobileNet, DenseNet, etc.

Given each possible candidate of analyte, the deep learning algorithm computes through layers of neurons via convolution filters and non-linear filters to extract high-level features that differentiate analyte against non-analytes. A layer of fully convolutional network will combine high-level features into classification results, which tells whether it is a true analyte or not, or the probability of being a analyte.

G) Applications, Bio/Chemical Biomarkers, and Health Conditions

The applications of the present invention include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In certain embodiments, the sample comprises a human body fluid. In certain embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled condensate.

In some embodiments, the sample is at least one of a biological sample, an environmental sample, and a biochemical sample.

The devices, systems and the methods in the present invention find use in a variety of different applications in various fields, where determination of the presence or absence, and/or quantification of one or more analytes in a sample are desired. For example, the subject method finds use in the detection of proteins, peptides, nucleic acids, synthetic compounds, inorganic compounds, and the like.

The various fields include, but not limited to, human, veterinary, agriculture, foods, environments, drug testing, and others.

In certain embodiments, the subject method finds use in the detection of nucleic acids, proteins, or other biomolecules in a sample. The methods can include the detection of a set of biomarkers, e.g., two or more distinct protein or nucleic acid biomarkers, in a sample. For example, the methods can be used in the rapid, clinical detection of two or more disease biomarkers in a biological sample, e.g., as can be employed in the diagnosis of a disease condition in a subject, or in the ongoing management or treatment of a disease condition in a subject, etc. As described above, communication to a physician or other health-care provider can better ensure that the physician or other health-care provider is made aware of, and cognizant of, possible concerns and can thus be more likely to take appropriate action.

The applications of the devices, systems and methods in the present inventions of employing a CROF device include, but are not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals. Some of the specific applications of the devices, systems and methods in the present invention are described now in further detail.

The applications of the present invention include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

An implementation of the devices, systems and methods in the present invention can include a) obtaining a sample, b) applying the sample to CROF device containing a capture agent that binds to an analyte of interest, under conditions suitable for binding of the analyte in a sample to the capture agent, c) washing the CROF device, and d) reading the CROF device, thereby obtaining a measurement of the amount of the analyte in the sample. In certain embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the CROF device can be placed in a microfluidic device and the applying step b) can include applying a sample to a microfluidic device comprising the CROF device.

In any embodiment, the reading step d) can include detecting a fluorescence or luminescence signal from the CROF device.

In any embodiment, the reading step d) can include reading the CROF device with a handheld device configured to read the CROF device. The handheld device can be a mobile phone, e.g., a smart phone.

In any embodiment, the CROF device can include a labeling agent that can bind to an analyte-capture agent complex on the CROF device.

In any embodiment, the devices, systems and methods in the present invention can further include, between steps c) and d), the steps of applying to the CROF device a labeling agent that binds to an analyte-capture agent complex on the CROF device, and washing the CROF device.

In any embodiment, the reading step d) can include reading an identifier for the CROF device. The identifier can be an optical barcode, a radio frequency ID tag, or combinations thereof.

In any embodiment, the devices, systems and methods in the present invention can further include applying a control sample to a control CROF device containing a capture agent that binds to the analyte, wherein the control sample includes a known detectable amount of the analyte, and reading the control CROF device, thereby obtaining a control measurement for the known detectable amount of the analyte in a sample.

In any embodiment, the sample can be a diagnostic sample obtained from a subject, the analyte can be a biomarker, and the measured amount of the analyte in the sample can be diagnostic of a disease or a condition.

In any embodiment, the devices, systems and methods in the present invention can further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In any embodiment, the devices, systems and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the applying step b) can include isolating miRNA from the sample to generate an isolated miRNA sample, and applying the isolated miRNA sample to the disk-coupled dots-on-pillar antenna (CROF device) array.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the CROF device array can include a plurality of capture agents that each binds to an environmental marker, and wherein the reading step d) can include obtaining a measure of the amount of the plurality of environmental markers in the sample. In any embodiment, the sample can be a foodstuff sample, wherein the analyte can be a foodstuff marker, and wherein the amount of the foodstuff marker in the sample can correlate with safety of the foodstuff for consumption.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained. In any embodiment, the CROF device array can include a plurality of capture agents that each binds to a foodstuff marker, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the CROF device can be employed. Suitable methods can include using a pipet, dropper, syringe, etc. In certain embodiments, when the CROF device is located on a support in a dipstick format, as described below, the sample can be applied to the CROF device by dipping a sample-receiving area of the dipstick into the sample.

A sample can be collected at one time, or at a plurality of times. Samples collected over time can be aggregated and/or processed (by applying to a CROF device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the CROF device to remove unbound sample components can be done in any convenient manner, as described above. In certain embodiments, the surface of the CROF device is washed using binding buffer to remove unbound sample components. Detectable labeling of the analyte can be done by any convenient method. The analyte can be labeled directly or indirectly. In direct labeling, the analyte in the sample is labeled before the sample is applied to the CROF device. In indirect labeling, an unlabeled analyte in a sample is labeled after the sample is applied to the CROF device to capture the unlabeled analyte, as described below.

The samples from a subject, the health of a subject, and other applications of the present invention are further described below. Exemplary samples, health conditions, and application are also disclosed in, e.g., U.S. Pub. Nos. 2014/0154668 and 2014/0045209, which are hereby incorporated by reference.

The present inventions find use in a variety of applications, where such applications are generally analyte detection applications in which the presence of a particular analyte in a given sample is detected at least qualitatively, if not quantitatively. Protocols for carrying out analyte detection assays are well known to those of skill in the art and need not be described in great detail here. Generally, the sample suspected of comprising an analyte of interest is contacted with the surface of a subject nanosensor under conditions sufficient for the analyte to bind to its respective capture agent that is tethered to the sensor. The capture agent has highly specific affinity for the targeted molecules of interest. This affinity can be antigen-antibody reaction where antibodies bind to specific epitope on the antigen, or a DNA/RNA or DNA/RNA hybridization reaction that is sequence-specific between two or more complementary strands of nucleic acids. Thus, if the analyte of interest is present in the sample, it likely binds to the sensor at the site of the capture agent and a complex is formed on the sensor surface. Namely, the captured analytes are immobilized at the sensor surface. After removing the unbounded analytes, the presence of this binding complex on the surface of the sensor (e.g. the immobilized analytes of interest) is then detected, e.g., using a labeled secondary capture agent.

Specific analyte detection applications of interest include hybridization assays in which the nucleic acid capture agents are employed and protein binding assays in which polypeptides, e.g., antibodies, are employed. In these assays, a sample is first prepared and following sample preparation, the sample is contacted with a subject nanosensor under specific binding conditions, whereby complexes are formed between target nucleic acids or polypeptides (or other molecules) that are complementary to capture agents attached to the sensor surface.

In one embodiment, the capture oligonucleotide is synthesized single strand DNA of 20-100 bases length, that is thiolated at one end. These molecules are are immobilized on the nanodevices' surface to capture the targeted single-strand DNA (which can be at least 50 bp length) that has a sequence that is complementary to the immobilized capture DNA. After the hybridization reaction, a detection single strand DNA (which can be of 20-100 bp in length) whose sequence are complementary to the targeted DNA's unoccupied nucleic acid is added to hybridize with the target. The detection DNA has its one end conjugated to a fluorescence label, whose emission wavelength are within the plasmonic resonance of the nanodevice. Therefore by detecting the fluorescence emission emanate from the nanodevices' surface, the targeted single strand DNA can be accurately detected and quantified. The length for capture and detection DNA determine the melting temperature (nucleotide strands will separate above melting temperature), the extent of misparing (the longer the strand, the lower the misparing).

One of the concerns of choosing the length for complementary binding depends on the needs to minimize misparing while keeping the melting temperature as high as possible. In addition, the total length of the hybridization length is determined in order to achieve optimum signal amplification.

A subject sensor can be employed in a method of diagnosing a disease or condition, comprising: (a) obtaining a liquid sample from a patient suspected of having the disease or condition, (b) contacting the sample with a subject nanosensor, wherein the capture agent of the nanosensor specifically binds to a biomarker for the disease and wherein the contacting is done under conditions suitable for specific binding of the biomarker with the capture agent; (c) removing any biomarker that is not bound to the capture agent; and (d) reading a light signal from biomarker that remain bound to the nanosensor, wherein a light signal indicates that the patient has the disease or condition, wherein the method further comprises labeling the biomarker with a light-emitting label, either prior to or after it is bound to the capture agent. As will be described in greater detail below, the patient can suspected of having cancer and the antibody binds to a cancer biomarker. In other embodiments, the patient is suspected of having a neurological disorder and the antibody binds to a biomarker for the neurological disorder.

The applications of the subject sensor include, but not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

The detection can be carried out in various sample matrix, such as cells, tissues, bodily fluids, and stool. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

In certain embodiments, a subject biosensor can be used diagnose a pathogen infection by detecting a target nucleic acid from a pathogen in a sample. The target nucleic acid can be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus, West Nile virus and Ebola virus. The present invention is not, however, limited to the detection of nucleic acid, e.g., DNA or RNA, sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

In some cases, the nanosensor can be employed to detect a biomarker that is present at a low concentration. For example, the nanosensor can be used to detect cancer antigens in a readily accessible bodily fluids (e.g., blood, saliva, urine, tears, etc.), to detect biomarkers for tissue-specific diseases in a readily accessible bodily fluid (e.g., a biomarkers for a neurological disorder (e.g., Alzheimer's antigens)), to detect infections (particularly detection of low titer latent viruses, e.g., HIV), to detect fetal antigens in maternal blood, and for detection of exogenous compounds (e.g., drugs or pollutants) in a subject's bloodstream, for example.

The following table provides a list of protein biomarkers that can be detected using the subject nanosensor (when used in conjunction with an appropriate monoclonal antibody), and their associated diseases. One potential source of the biomarker (e.g., "CSF"; cerebrospinal fluid) is also indicated in the table. In many cases, the subject biosensor can detect those biomarkers in a different bodily fluid to that indicated. For example, biomarkers that are found in CSF can be identified in urine, blood or saliva.

H) Utility

The subject method finds use in a variety of different applications where determination of the presence or absence, and/or quantification of one or more analytes in a sample are desired. For example, the subject method finds use in the detection of proteins, peptides, nucleic acids, synthetic compounds, inorganic compounds, and the like.

In certain embodiments, the subject method finds use in the detection of nucleic acids, proteins, or other biomolecules in a sample. The methods can include the detection of a set of biomarkers, e.g., two or more distinct protein or nucleic acid biomarkers, in a sample. For example, the methods can be used in the rapid, clinical detection of two or more disease biomarkers in a biological sample, e.g., as can be employed in the diagnosis of a disease condition in a subject, or in the ongoing management or treatment of a disease condition in a subject, etc. As described above, communication to a physician or other health-care provider can better ensure that the physician or other health-care provider is made aware of, and cognizant of, possible concerns and can thus be more likely to take appropriate action.

The applications of the devices, systems and methods in the present invention of employing a CROF device include, but are not limited to, (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals. Some of the specific applications of the devices, systems and methods in the present invention are described now in further detail.

I) Diagnostic Method

In certain embodiments, the subject method finds use in detecting biomarkers. In certain embodiments, the devices, systems and methods in the present invention of using CROF are used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like. Thus, the sample, e.g. a diagnostic sample, can include various fluid or solid samples.

In some instances, the sample can be a bodily fluid sample from a subject who is to be diagnosed. In some instances, solid or semi-solid samples can be provided. The sample can include tissues and/or cells collected from the subject. The sample can be a biological sample. Examples of biological samples can include but are not limited to, blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk, exhaled condensate and/or other excretions. The samples can include nasopharyngeal wash. Nasal swabs, throat swabs, stool samples, hair, finger nail, ear wax, breath, and other solid, semi-solid, or gaseous samples can be processed in an extraction buffer, e.g., for a fixed or variable amount of time, prior to their analysis. The extraction buffer or an aliquot thereof can then be processed similarly to other fluid samples if desired. Examples of tissue samples of the subject can include but are not limited to, connective tissue, muscle tissue, nervous tissue, epithelial tissue, cartilage, cancerous sample, or bone.

In some instances, the subject from which a diagnostic sample is obtained can be a healthy individual, or can be an individual at least suspected of having a disease or a health condition. In some instances, the subject can be a patient.

In certain embodiments, the CROF device includes a capture agent configured to specifically bind a biomarker in a sample provided by the subject. In certain embodiments, the biomarker can be a protein. In certain embodiments, the biomarker protein is specifically bound by an antibody capture agent present in the CROF device. In certain embodiments, the biomarker is an antibody specifically bound by an antigen capture agent present in the CROF device. In certain embodiments, the biomarker is a nucleic acid specifically bound by a nucleic acid capture agent that is complementary to one or both strands of a double-stranded nucleic acid biomarker, or complementary to a single-stranded biomarker. In certain embodiments, the biomarker is a nucleic acid specifically bound by a nucleic acid binding protein. In certain embodiments, the biomarker is specifically bound by an aptamer.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers can influence the choices of drug treatment or administration regimes given to an individual. In evaluating potential drug therapies, a biomarker can be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject method. Furthermore, the early detection of biomarkers associated with diseases is facilitated by the high sensitivity of the devices, systems and methods in the present invention, as described above. Due to the capability of detecting multiple biomarkers with a mobile device, such as a smartphone, combined with sensitivity, scalability, and ease of use, the presently disclosed method finds use in portable and point-of-care or near-patient molecular diagnostics.

In certain embodiments, the subject method finds use in detecting biomarkers for a disease or disease state. In certain instances, the subject method finds use in detecting biomarkers for the characterization of cell signaling pathways and intracellular communication for drug discovery and vaccine development. For example, the subject method can be used to detect and/or quantify the amount of biomarkers in diseased, healthy or benign samples. In certain embodiments, the subject method finds use in detecting biomarkers for an infectious disease or disease state. In some cases, the biomarkers can be molecular biomarkers, such as but not limited to proteins, nucleic acids, carbohydrates, small molecules, and the like.

The subject method find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

In certain embodiments, a subject biosensor can be used diagnose a pathogen infection by detecting a target nucleic acid from a pathogen in a sample. The target nucleic acid can be, for example, from a virus that is selected from the group comprising human immunodeficiency virus 1 and 2 (HIV-1 and HIV-2), human T-cell leukaemia virus and 2 (HTLV-1 and HTLV-2), respiratory syncytial virus (RSV), adenovirus, hepatitis B virus (HBV), hepatitis C virus (HCV), Epstein-Barr virus (EBV), human papillomavirus (HPV), varicella zoster virus (VZV), cytomegalovirus (CMV), herpes-simplex virus 1 and 2 (HSV-1 and HSV-2), human herpesvirus 8 (HHV-8, also known as Kaposi sarcoma herpesvirus) and flaviviruses, including yellow fever virus, dengue virus, Japanese encephalitis virus, West Nile virus and Ebola virus. The present invention is not, however, limited to the detection of nucleic acid, e.g., DNA or RNA, sequences from the aforementioned viruses, but can be applied without any problem to other pathogens important in veterinary and/or human medicine.

Human papillomaviruses (HPV) are further subdivided on the basis of their DNA sequence homology into more than 70 different types. These types cause different diseases. HPV types 1, 2, 3, 4, 7, 10 and 26-29 cause benign warts. HPV types 5, 8, 9, 12, 14, 15, 17 and 19-25 and 46-50 cause lesions in patients with a weakened immune system. Types 6, 11, 34, 39, 41-44 and 51-55 cause benign acuminate warts on the mucosae of the genital region and of the respiratory tract. HPV types 16 and 18 are of special medical interest, as they cause epithelial dysplasias of the genital mucosa and are associated with a high proportion of the invasive carcinomas of the cervix, vagina, vulva and anal canal. Integration of the DNA of the human papillomavirus is considered to be decisive in the carcinogenesis of cervical cancer. Human papillomaviruses can be detected for example from the DNA sequence of their capsid proteins L1 and L2. Accordingly, the method of the present invention is especially suitable for the detection of DNA sequences of HPV types 16 and/or 18 in tissue samples, for assessing the risk of development of carcinoma.

Other pathogens that can be detected in a diagnostic sample using the devices, systems and methods in the present invention include, but are not limited to: Varicella zoster; *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumoniae, Haemophilus influenzae, Staphylococcus simulans, Streptococcus pneumoniae* and *Candida albicans*; gonorrhea (*Neisseria gorrhoeae*), syphilis (*Treponena pallidum*), clamydia (*Clamyda tracomitis*), nongonococcal urethritis (*Ureaplasm urealyticum*), chancroid (*Haemophilus ducreyi*), trichomoniasis (*Trichomonas vaginalis*); *Pseudomonas aeruginosa*, methicillin-resistant *Staphlococccus aureus* (MSRA), *Klebsiella pneumoniae, Haemophilis influenzae, Staphylococcus aureus, Stenotrophomonas maltophilia, Haemophilis parainfluenzae, Escherichia coli, Enterococcus faecalis, Serratia marcescens, Haemophilis parahaemolyticus, Enterococcus cloacae, Candida albicans, Moraxiella catarrhalis, Streptococcus pneumoniae, Citrobacter freundii, Enterococcus faecium, Klebsella oxytoca, Pseudomonas fluorscens, Neiseria meningitidis, Streptococcus pyogenes, Pneumocystis carinii, Klebsella pneumoniae Legionella pneumophila, Mycoplasma pneumoniae*, and *Mycobacterium tuberculosis*, etc.

In some cases, the CROF device can be employed to detect a biomarker that is present at a low concentration. For example, the CROF device can be used to detect cancer antigens in a readily accessible bodily fluids (e.g., blood, saliva, urine, tears, etc.), to detect biomarkers for tissue-specific diseases in a readily accessible bodily fluid (e.g., a biomarkers for a neurological disorder (e.g., Alzheimer's antigens)), to detect infections (particularly detection of low titer latent viruses, e.g., HIV), to detect fetal antigens in maternal blood, and for detection of exogenous compounds (e.g., drugs or pollutants) in a subject's bloodstream, for example.

One potential source of the biomarker (e.g., "CSF"; cerebrospinal fluid) is also indicated in the table. In many cases, the subject biosensor can detect those biomarkers in a different bodily fluid to that indicated. For example, biomarkers that are found in CSF can be identified in urine, blood or saliva. It will also be clear to one with ordinary skill in the art that the subject CROF devices can be configured to capture and detect many more biomarkers known in the art that are diagnostic of a disease or health condition.

A biomarker can be a protein or a nucleic acid (e.g., mRNA) biomarker, unless specified otherwise. The diagnosis can be associated with an increase or a decrease in the level of a biomarker in the sample, unless specified otherwise. Lists of biomarkers, the diseases that they can be used to diagnose, and the sample in which the biomarkers can be detected are described in Tables 1 and 2 of U.S. provisional application Ser. No. 62/234,538, filed on Sep. 29, 2015, which application is incorporated by reference herein.

In some instances, the devices, systems and methods in the present invention is used to inform the subject from whom the sample is derived about a health condition thereof. Health conditions that can be diagnosed or measured by the devices, systems and methods in the present invention, device and system include, but are not limited to: chemical balance; nutritional health; exercise; fatigue; sleep; stress; prediabetes; allergies; aging; exposure to environmental toxins, pesticides, herbicides, synthetic hormone analogs; pregnancy; menopause; and andropause. Table 3 of U.S. provisional application Ser. No. 62/234,538, filed on Sep. 29, 2015, which application is incorporated by reference herein, provides a list of biomarker that can be detected using the present CROF device (when used in conjunction with an appropriate monoclonal antibody, nucleic acid, or other capture agent), and their associated health conditions.

J) Kits

Aspects of the present disclosure include a kit that find use in performing the devices, systems and methods in the present invention, as described above. In certain embodiments, the kit includes instructions for practicing the subject methods using a hand held device, e.g., a mobile phone. These instructions can be present in the subject kits in a variety of forms, one or more of which can be present in the kit. One form in which these instructions can be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that can be present is a website address which can be used via the Internet to access the information at a removed site. The kit can further include a software for implementing a method for measuring an analyte on a device, as described herein, provided on a computer readable medium. Any convenient means can be present in the kits.

In certain embodiments, the kit includes a detection agent that includes a detectable label, e.g. a fluorescently labeled antibody or oligonucleotide that binds specifically to an analyte of interest, for use in labeling the analyte of interest. The detection agent can be provided in a separate container as the CROF device, or can be provided in the CROF device. In certain embodiments, the kit includes a control sample that includes a known detectable amount of an analyte that is to be detected in the sample. The control sample can be provided in a container, and can be in solution at a known concentration, or can be provided in dry form, e.g., lyophilized or freeze dried. The kit can also include buffers for use in dissolving the control sample, if it is provided in dry form.

Aspects

Aspect 1. A device, comprising:
- a substrate having a plurality of detection areas to receive at least a portion of a sample having an analyte or suspected of having an analyte; and
- at least one reference marker adjacent to at least one of the of detection areas, wherein:
- each of the detection areas detects a specific analyte; and
- the at least one reference marker is a scale marker, a shape marker, a color marker, or a combination thereof.

Aspect 2. The device of Aspect 1, wherein the plurality of detection areas receives at least a portion of a sample in a vertical flow or a lateral flow of the sample.

Aspect 3. The device of Aspect 1, wherein each of the detection areas detects a different and specific analyte.

Aspect 4. The device of Aspect 1, wherein the shape, separation distance, and size of each of the detection areas can be same or different.

Aspect 5. The device of Aspect 1, wherein one of the detection areas for one assay has a shape selected from round, polygonal, circular, square, rectangular, oval, elliptical, or any superpositional combination thereof.

Aspect 6. The device of Aspect 1, wherein one of the detection areas for one assay has a length dimension of size of 0.1 mm, 0.2 mm, 0.5 mm, 1 mm, 2 mm, 5 mm, 10 mm, 20 mm, or an intermediate value or range.

Aspect 7. The device of Aspect 1, wherein the separation distance between each of the detection areas is 0.1 mm, 0.2 mm, 0.5 mm, 1 mm, 2 mm, 5 mm, 10 mm, 20 mm, or an intermediate value or range.

Aspect 8. The device of Aspect 1, wherein the plurality of detection areas is from 2 to about 50.

Aspect 9. The device of Aspect 1, wherein the plurality of detection areas is from 3 to about 20.

Aspect 10. The device of Aspect 1, wherein the at least one reference marker is from 1 to about 10 reference markers.

Aspect 11. The device of Aspect 1, wherein at least one of the scale markers has at least one length dimension of 2 μm, 10 um, 20 μm, 50 um, 100 μm, or an intermediate value or range.

Aspect 12. The device of Aspect 1, wherein at least one of the scale markers has a length dimension of 0.1 mm, 0.2 mm, 0.5 mm, 1 mm, 2 mm, 5 mm, 10 mm, or an intermediate value or range.

Aspect 13. The device of Aspect 1, wherein the shape marker has a shape selected from round, polygonal, circular, square, rectangular, oval, elliptical, or any super-positional combination.

Aspect 14. The device of Aspect 1, wherein the color marker has a color match in a colorimetric assay.

Aspect 15. The device of Aspect 1, wherein the color marker has a color that matches the central absorption wavelength of a reactive dye or the color of the dye in the device.

Aspect 16. The device of Aspect 1, wherein the color marker has a color that has a central absorption wavelength of from 400 nm to 700 nm.

Aspect 17. The device of Aspect 1, wherein the color marker has a color that has more than one central absorption wavelength of from 400 nm to 700 nm.

Aspect 18. The device of Aspect 1, wherein the color marker has a color that has an absorption wavelength bandwidth of 20 nm, 50 nm, 80 nm, 100 nm, 150 nm, 200 nm, including intermediate values and ranges.

Aspect 19. An imaging system, comprising:
- the device of Aspect 1;
- an imager for capturing an image of at least one of the detection areas and at least one reference marker; and
- an image analyzer for analyzing the image of at least one of the detection areas and at least one reference marker.

Aspect 20. The imaging system of Aspect 19, wherein the imager is a camera and a light source.

Aspect 21. The imaging system of Aspect 20, wherein the light source includes an optical fiber having side wall light leakage.

Aspect 22. The imaging system of Aspect 19, wherein the imager has a field of view (FOV) of 0.1 mm, 0.2 mm, 0.5 mm, 1 mm, 2 mm, 5 mm, 10 mm, 20 mm, 50 mm, or an intermediate value or range.

Aspect 23. The imaging system of Aspect 19, wherein the imager has a resolution of 1 μm, 2 um, 5 μm, 10 um, 20 μm, 100 um, 200 μm, or an intermediate value or range.

Aspect 24. The imaging system of Aspect 19, wherein the imager includes a filter to enhance certain wavelength lights.

Aspect 25. The imaging system of Aspect 19, wherein the imager includes a set of polarizers to enhance image quality or enhance image contrast.

Aspect 26. The imaging system of Aspect 19, wherein the imager includes using a RAW image file format to process a recorded image.

Aspect 27. The imaging system of Aspect 19, wherein the imager comprises a smartphone.

Aspect 28. An assay method, comprising:
- contacting the device of Aspect 1 and a sample having an analyte or suspected of having an analyte;
- imaging the substrate having a plurality of detection areas that have been contacted by the sample after a period of time to form an image; and
- analyzing the image and at least one reference marker.

Aspect 29. The assay method of Aspect 28, wherein the assay method is an enzymatic reaction assay.

Aspect 30. The assay method of Aspect 28, wherein the assay method is an immunosorbent assay.

Aspect 31. The assay method of Aspect 28, wherein the assay method is a colorimetric method, a fluorescence method, or a combination thereof.

Aspect 32. The assay method of Aspect 28, wherein analyzing the image and at least one reference marker comprises using imaging software to distinguish and correct non-uniform signal distribution in the detection areas.

Aspect 33. The assay method of Aspect 32, wherein the non-uniform signal distribution includes at least one of a signal average, a signal medium, a signal standard deviation, a distribution slope, and are used in a true signal analysis.

Aspect 34. The assay method of Aspect 28, wherein analyzing the image and at least one reference marker comprises using imaging software to distinguish and correct local defects in the image of the detection area including one or more of bubbles, local particle aggregations, foreign particles, unexpected colors, device non-uniformity, or a combination thereof.

Aspect 35. The assay method of Aspect 28, wherein analyzing the image and at least one reference marker comprises using imaging software to remove defects from the final signal.

Aspect 36. The assay method of Aspect 28, wherein analyzing the image and at least one reference marker comprises using imaging software to distinguish and correct a signal or a signal boundary from a background image.

Aspect 37. The assay method of Aspect 28, wherein the boundary of a signal area to detect a background area has a width of 5 μm, 10 um, 20 μm, 50 um, 100 μm, 200 um, 500 μm, 1 mm, or an intermediate value or range.

Aspect 38. The assay method of Aspect 28, wherein the signal in the detection area is analyzed using red, green, blue, hue, saturation, brightness, grey channel, or a combination thereof.

We claim:

1. A device for a lateral or vertical flow assay, comprising:

a substrate having a plurality of detection areas to receive at least a portion of a sample having an analyte or suspected of having an analyte;

at least one first reference marker that is adjacent to at least one of the detection areas; and at least one second reference marker disposed within at least one of the detection areas, wherein:

each of the detection areas detects a specific analyte;

the at least one first reference marker and the at least one second reference marker each independently is a scale marker, a shape marker, a color marker, or a combination thereof;

the detection areas are arranged in a linear configuration for the lateral flow assay or a layered configuration for the vertical flow assay; and the at least one second reference marker comprises a plurality of periodic pillars or spacers disposed within the at least one of the detection areas, and the plurality of periodic pillars or spacers having a period of 50 μm to 200 μm and each of the periodic pillars or spacers having a size of 10 μm to 50 μm.

2. The device of claim 1, wherein each of the detection areas detects a different and specific analyte.

3. The device of claim 1, wherein the shape, separation distance, and size of each of the detection areas can be same or different.

4. The device of claim 1, wherein one of the detection areas for one assay has a shape selected from round, polygonal, circular, square, rectangular, oval, elliptical, or any superpositional combination thereof.

5. The device of claim 1, wherein one of the detection areas for one assay has a length dimension of size of 0.1 mm, 0.2 mm, 0.5 mm, 1 mm, 2 mm, 5 mm, 10 mm, 20 mm, or an intermediate value or range.

6. The device of claim 1, wherein the separation distance between each of the detection areas is 0.1 mm, 0.2 mm, 0.5 mm, 1 mm, 2 mm, 5 mm, 10 mm, 20 mm, or in a range between any two of the above distances.

7. The device of claim 1, wherein the plurality of detection areas is from 2 to about 50.

8. The device of claim 1, wherein the plurality of detection areas is from 3 to about 20.

9. The device of claim 1, wherein the at least one reference marker is from 1 to about 10 reference markers.

10. The device of claim 1, wherein at least one of the scale markers has at least one length dimension of 2 μm, 10 um, 20 μm, 50 μm, 100 μm, or in a range between any two of the above length dimensions.

11. The device of claim 1, wherein at least one of the scale markers has a length dimension of 0.1 mm, 0.2 mm, 0.5 mm, 1 mm, 2 mm, 5 mm, 10 mm, or in a range between any two of the above length dimensions.

12. The device of claim 1, wherein the shape marker has a shape selected from round, polygonal, circular, square, rectangular, oval, elliptical, or any super-positional combination thereof.

13. The device of claim 1, wherein the color marker has a color match in a colorimetric assay.

14. The device of claim 1, wherein the color marker has a color that matches the central absorption wavelength of a reactive dye or the color of the dye in the device.

15. The device of claim 1, wherein the color marker has a color that has a central absorption wavelength of from 400 nm to 700 nm.

16. The device of claim 1, wherein the color marker has a color that has more than one central absorption wavelength of from 400 nm to 700 nm.

17. The device of claim 1, wherein the color marker has a color that has an absorption wavelength bandwidth of 20 nm, 50 nm, 80 nm, 100 nm, 150 nm, 200 nm, in a range between any two of the above absorption wavelength bandwidth.

18. An imaging system, comprising:

the device of claim 1;

an imager for capturing an image of at least one of the detection areas and at least one reference marker; and an image analyzer for analyzing the image of at least one of the detection areas and at least one reference marker, wherein the image analyzer is configured to detect one or more local defects in the image of the at least one detection area, remove portions of the image corresponding to the one or more local defects from analysis, extract one or more image features from a remaining portion of the image, and calculate an analyte concentration based on the extracted one or more image features.

19. The imaging system of claim 18, wherein the imager comprises a camera and a light source.

20. An assay method, comprising:

contacting the device of claim 1 with a sample having an analyte or suspected of having an analyte;

imaging the substrate after a period of time to obtain an image; and analyzing the image and the at least one first reference marker or the at least one second reference marker, wherein analyzing the image comprises detecting one or more local defects in at least one detection area, removing portions of the image corresponding to the one or more local defects from analysis, extracting one or more image features from a remaining portion of the image, and calculating an analyte concentration based on the extracted one or more image features.

* * * * *